US012635946B2

(12) United States Patent
Huang et al.

(10) Patent No.: US 12,635,946 B2
(45) Date of Patent: May 26, 2026

(54) PATCH AND METHOD FOR USING A PATCH

(71) Applicant: Bionime Corporation, Taichung City (TW)

(72) Inventors: Chun-Mu Huang, Taichung City (TW); Chieh-Hsing Chen, Taichung City (TW); Shiang-Yu Wu, Taichung City (TW)

(73) Assignee: Bionime Corporation, Taichung City (TW)

( * ) Notice: Subject to any disclaimer, the term of this patent is extended or adjusted under 35 U.S.C. 154(b) by 1151 days.

(21) Appl. No.: 17/200,170

(22) Filed: Mar. 12, 2021

(65) Prior Publication Data

US 2021/0282711 A1     Sep. 16, 2021

Related U.S. Application Data

(60) Provisional application No. 63/135,084, filed on Jan. 8, 2021.

(30) Foreign Application Priority Data

Mar. 13, 2020    (TW) ................................. 109108480

(51) Int. Cl.
*A61B 5/00*            (2006.01)
(52) U.S. Cl.
CPC ........ *A61B 5/6833* (2013.01); *A61B 5/68335* (2017.08)
(58) Field of Classification Search
CPC .............. A61B 5/6833; A61B 5/68335; A61B 5/14532; A61B 5/14503; A61B 5/1451;
(Continued)

(56) References Cited

U.S. PATENT DOCUMENTS

| | | | |
|---|---|---|---|
| 6,295,463 | B1 | 9/2001 | Stenzler |
| 2012/0071731 | A1 | 3/2012 | Gottesman |

(Continued)

FOREIGN PATENT DOCUMENTS

| JP | 2018102576 A | 7/2018 | |
|---|---|---|---|
| WO | WO-2007140785 A1 * | 12/2007 | ............. A61F 13/02 |

OTHER PUBLICATIONS

Machine Translation of JP 2018-102576A (Year: 2018).*

*Primary Examiner* — Patricia L. Nordmeyer
(74) *Attorney, Agent, or Firm* — Bever, Hoffman & Harms, LLP

(57)            ABSTRACT

A patch for increasing an adhesive strength of a physiological parameter detection device on a skin surface includes a backing and a peelable sheet. The backing is disposed with an adhesive layer having an adhesive surface. The adhesive surface includes a central adhesive portion and an outer adhesive portion, and, upon the central adhesive portion is exposed, the patch is caused to apply a pressure toward the physiological parameter detection device so as to allow the central adhesive portion to be adhered to a top surface of the physiological parameter detection device. The peelable sheet, which is detachably adhered to the adhesive surface for preserving the adhesive surface, includes an inner peelable portion and an outer peelable portion. After the central adhesive portion is exposed, the outer peelable sheet continuously provides a supporting force for the backing so as to allow the backing to be easily and evenly adhered.

14 Claims, 36 Drawing Sheets

(58) Field of Classification Search
CPC ............... A61B 5/6843; A61B 5/14514; A61F
13/0259
See application file for complete search history.

(56) References Cited

U.S. PATENT DOCUMENTS

| | | |
|---|---|---|
| 2014/0206977 A1 | 7/2014 | Bahney et al. |
| 2015/0073325 A1 | 3/2015 | Oeeluno |
| 2015/0080697 A1 | 3/2015 | Gilmore et al. |
| 2016/0058380 A1 | 3/2016 | Lee et al. |
| 2017/0128010 A1* | 5/2017 | Kube .................... A61F 13/023 |
| 2017/0156594 A1 | 6/2017 | Stivoric et al. |

* cited by examiner

513

514

PATCH AND METHOD FOR USING A PATCH

CROSS REFERENCE TO RELATED APPLICATIONS

The application claims the benefits of Taiwan Patent Application No. 109108480, filed on Mar. 13, 2020, at the Taiwan Intellectual Property Office, and U.S. provisional patent application Ser. No. 63/135,084 entitled "PATCH, REINFOREMENT PATCH AND PHYSIOLOGICAL SIGNAL MONITORING DEVICE USING THE SAME", filed on Jan. 8, 2021, the disclosures of which are incorporated herein in their entirety by reference.

FIELD OF THE INVENTION

The present invention relates to a patch and a method for using a patch. More particularly, the present invention relates to a patch and a method for using a patch suitable for a physiological parameter detection device.

BACKGROUND OF THE INVENTION

A patch-type physiological parameter detection device uses a base patch to adhere the physiological parameter detection device to a skin surface of a user. Considering the durability and comfort when adhering the physiological parameter detection device to the skin surface, and in order to prevent the base patch from falling off during use, a patch having a greater area is usually covered on the base patch to increase the strength of the base patch of the physiological parameter detection device (such as a transmitter) adhered to the skin.

For example, a traditional blood glucose management uses a blood glucose monitor system (BGMS). Under this system, in order to monitor the glucose concentration of interstitial fluids, a diabetic patient must take blood by needling the skin several times a day for measurement. The American Diabetes Association (ADA) recommends that it is best to measure the glucose concentration three times a day or more, but the patient will find it hard to endure the pain and inconvenience. Therefore, in order to alleviate the suffering of the patient, continuous glucose monitoring (CGM) was developed. Its detection principle is that a soft needle, that is, a sensor, is implanted under the skin to continuously test the glucose level in the interstitial fluid, and the retention period can be up to fourteen days, which greatly reduces the burden on the patient. The continuous blood glucose monitor is a patch-type physiological parameter detection device.

Considering the comfort, the patch used in the aforementioned patch-type physiological parameter detection device is generally made of a relatively soft material. However, this kind of material easily bunches up and gets wrinkled, which makes it difficult for a user to adhere it to the skin smoothly, especially when it is applied with one hand.

In view of this, it is necessary to develop a patch that easily and smoothly adheres to the skin.

SUMMARY OF THE INVENTION

In accordance with one aspect of the present invention, a patch for increasing an adhesive strength of a physiological parameter detection device on a skin surface is disclosed, and includes a backing and peelable sheet. The backing disposes thereon an adhesive layer having an adhesive surface, wherein the adhesive surface includes a central adhesive portion and an outer adhesive portion; and upon the central adhesive portion is exposed, the patch is caused to apply a pressure toward the physiological parameter detection device so as to allow the central adhesive portion to be adhered to a top surface of the physiological parameter detection device. The peelable sheet is detachably adhered to the adhesive surface for preserving the adhesive surface, and includes an inner peelable portion and an outer peelable portion, wherein after the central adhesive portion is exposed, the outer peelable sheet continuously provides a supporting force for the backing so as to allow the backing to be easily and evenly adhered.

In accordance with another aspect of the present invention, a method for using a patch is disclosed. The patch is cooperated with a physiological parameter detection device having a base patch. The method includes the following steps:

A patch including a backing and a peelable sheet is provided, wherein the backing is disposed with an adhesive layer having an adhesive surface; the adhesive surface includes a central adhesive portion and an outer adhesive portion; and the peelable sheet is detachably adhered to the adhesive surface for preserving the adhesive surface and includes an inner peelable portion and an outer peelable portion. The physiological parameter detection device is adhered to a skin surface through the base patch. The inner peelable portion is moved away from the central adhesive portion to at least expose the central adhesive portion. Upon a supporting force provided by the outer peelable portion for the backing, the central adhesive portion is adhered to a top surface of the physiological parameter detection device. The outer peelable portion is peeled off to expose the outer adhesive portion. In addition, the outer adhesive portion is adhered to the skin surface.

DETAILED DESCRIPTION OF THE PREFERRED EMBODIMENTS

Figure 1:
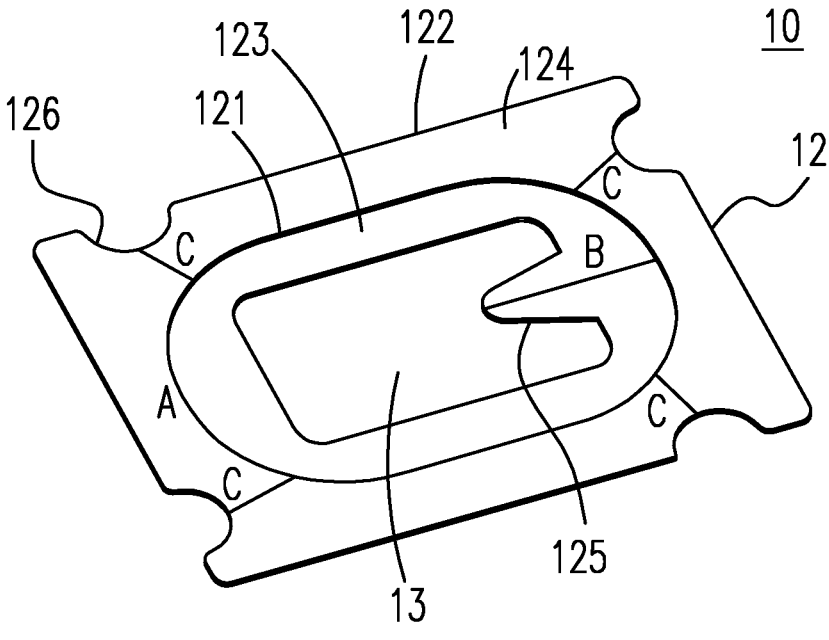
FIG. 1 shows a rear view of a patch according to an embodiment of the present invention.

The technical content, features and effects of the present invention will be clearly presented by the following detailed descriptions of preferred embodiments.

Please refer to FIGS. 1-16. The first embodiment of the present invention provides a patch system 1. First please refer to FIGS. 7-11, the patch system 1 includes a physiological parameter detection device 21; a backing 111; and a peelable sheet 12. The physiological parameter detection device 21 has a base patch 22, and the physiological parameter detection device 21 is adhered to a skin surface via the base patch 22. The physiological parameter detection device 21 may be a combination of a transmitter, a sensor, and a base in a continuous glucose monitoring system.

Figure 3:
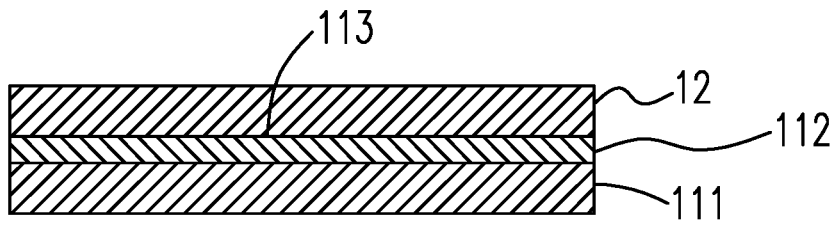
FIG. 3 shows a longitudinal section of the patch according to an embodiment of the present invention.

Please refer to FIG. 3. An adhesive layer 112 having an adhesive surface 113 is disposed on the backing 111. The backing 111 is adhered to the skin surface via the adhesive surface 113. The peelable sheet 12 is detachably adhered to the adhesive surface 113. The peelable sheet 12 is used to preserve the adhesive surface 113 of the backing 111 and provide a supporting (stretching-up) force to the backing 111.

Please refer to FIG. 1. The peelable sheet 12 includes an inner peelable sheet 121 and an outer peelable sheet 122, wherein the both sheets are relatively easily peelable off from the adhesive surface 113.

Figure 5:
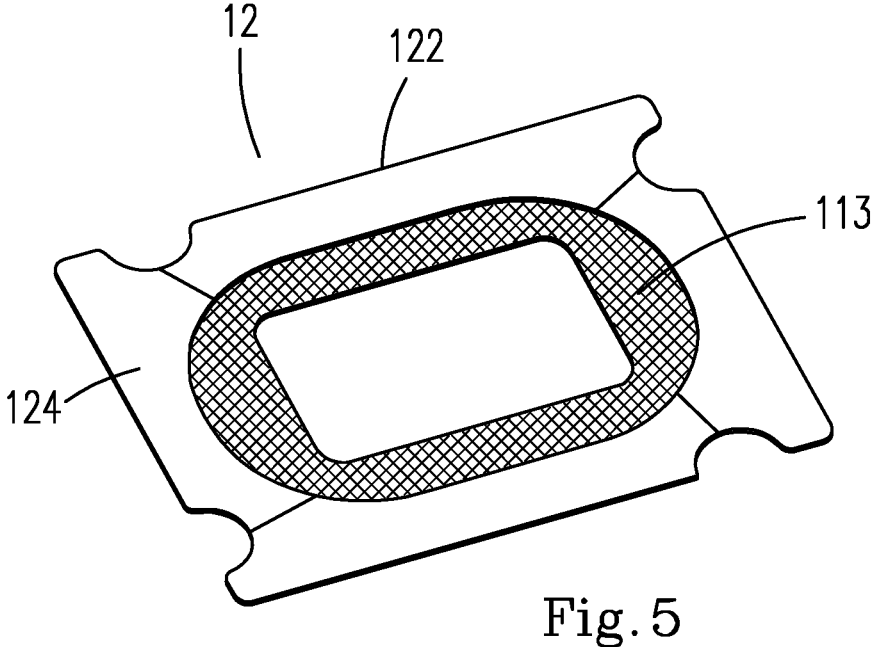
FIG. 5 shows a use state of the patch according to an embodiment of the present invention.
Figure 6:
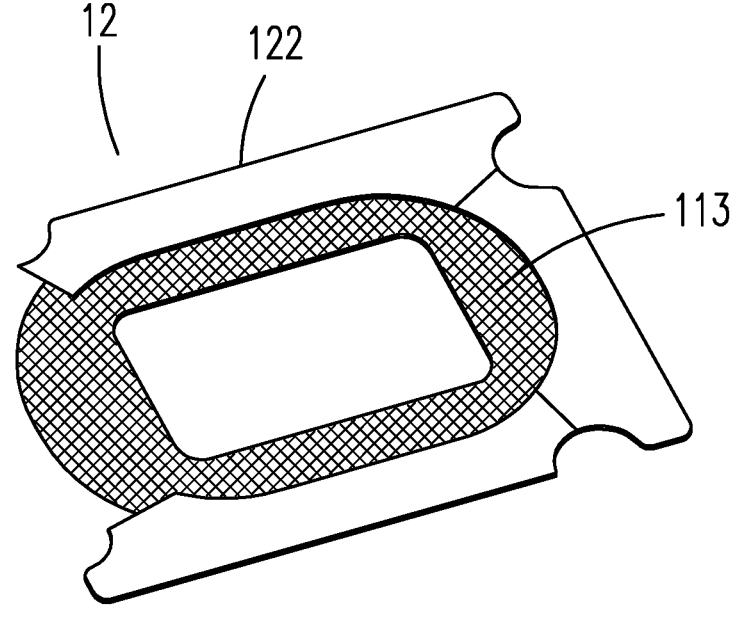
FIG. 6 shows a use state of the patch according to an embodiment of the present invention.
Figure 7:
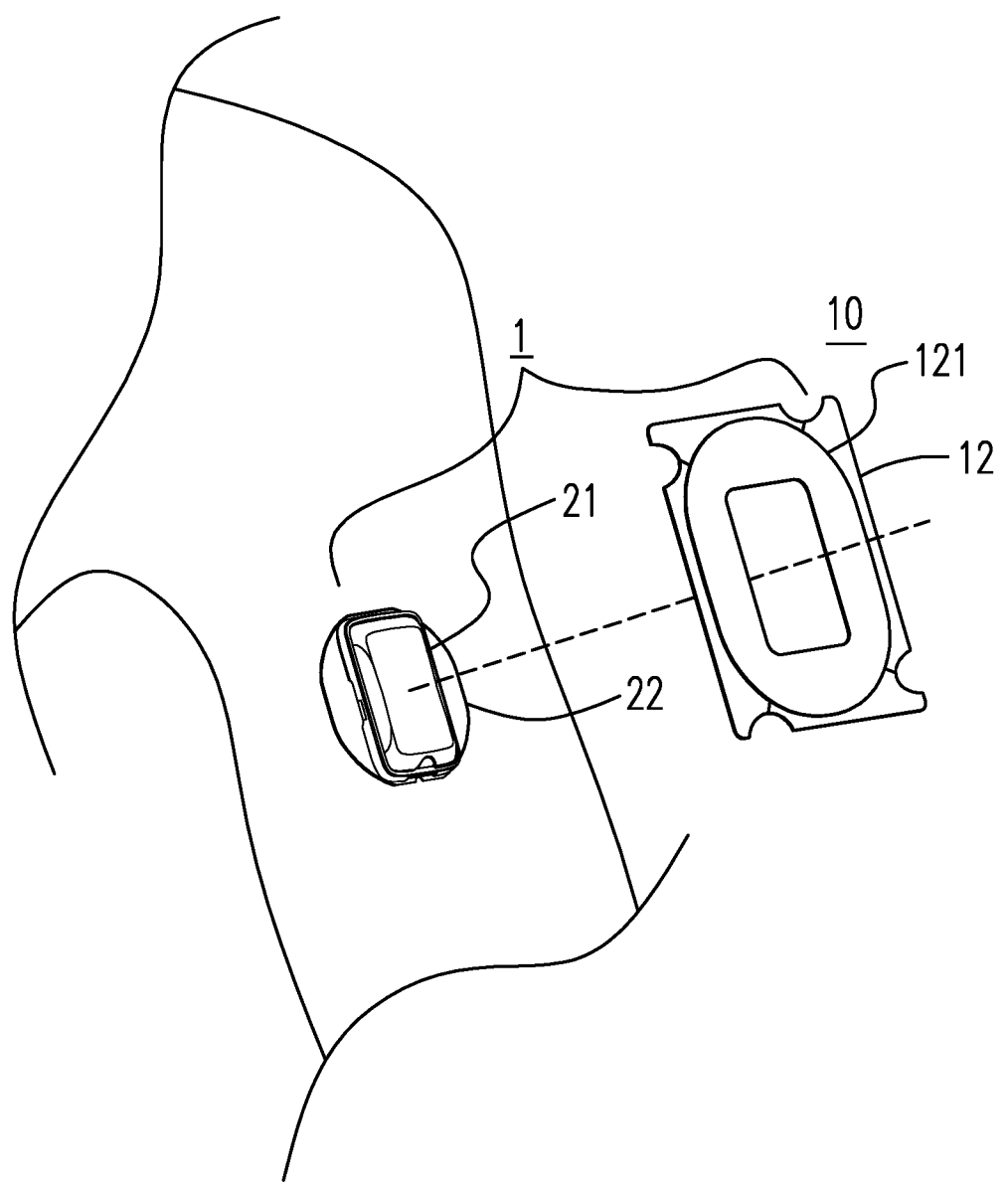
FIG. 7 shows a patch system according to an embodiment of the present invention.
Figure 8:
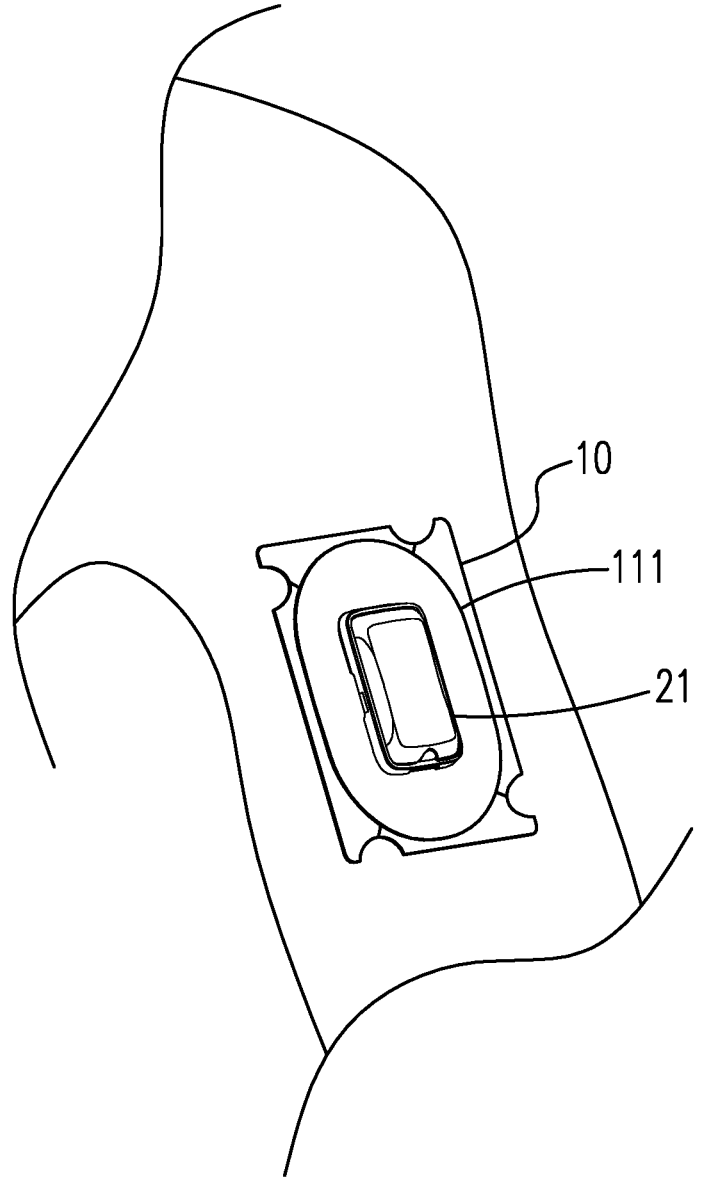
FIG. 8 shows the patch system according to an embodiment of the present invention.
Figure 9:
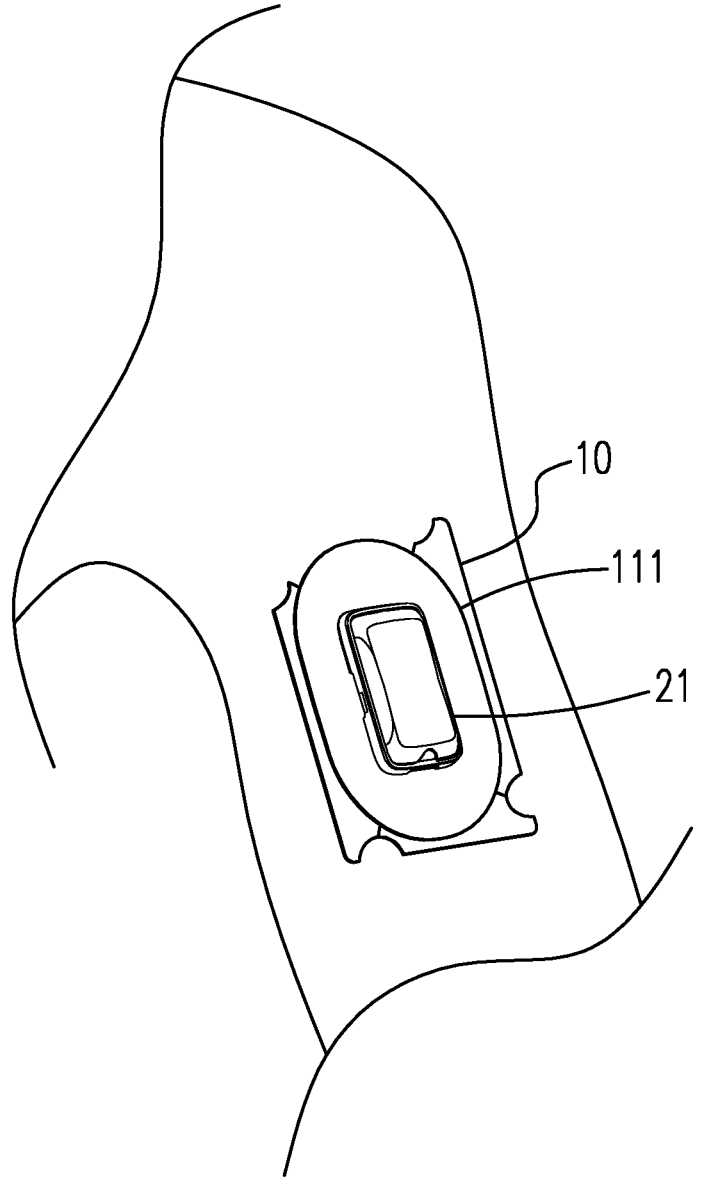
FIG. 9 shows the patch system according to an embodiment of the present invention.
Figure 10:
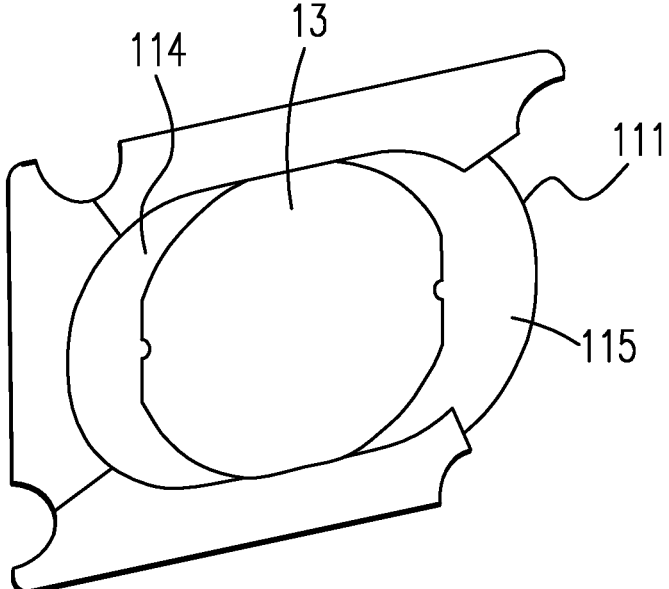
FIG. 10 shows the patch system according to an embodiment of the present invention.
Figure 11:
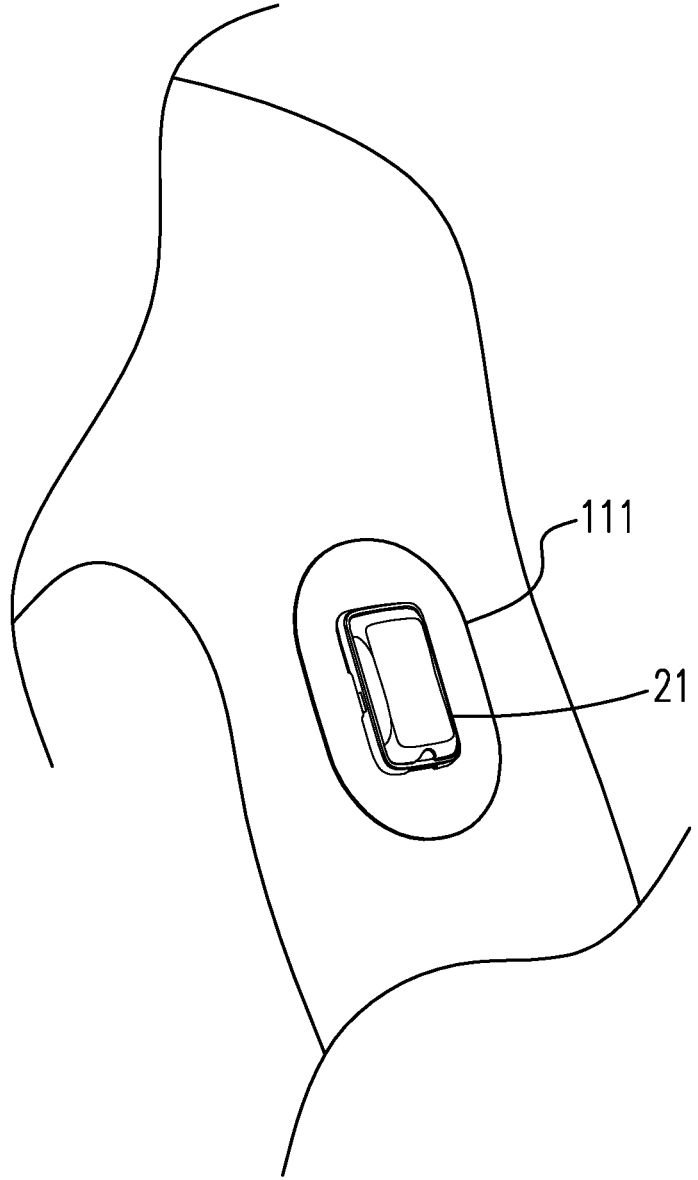
FIG. 11 shows the patch system according to an embodiment of the present invention.
Figure 12:
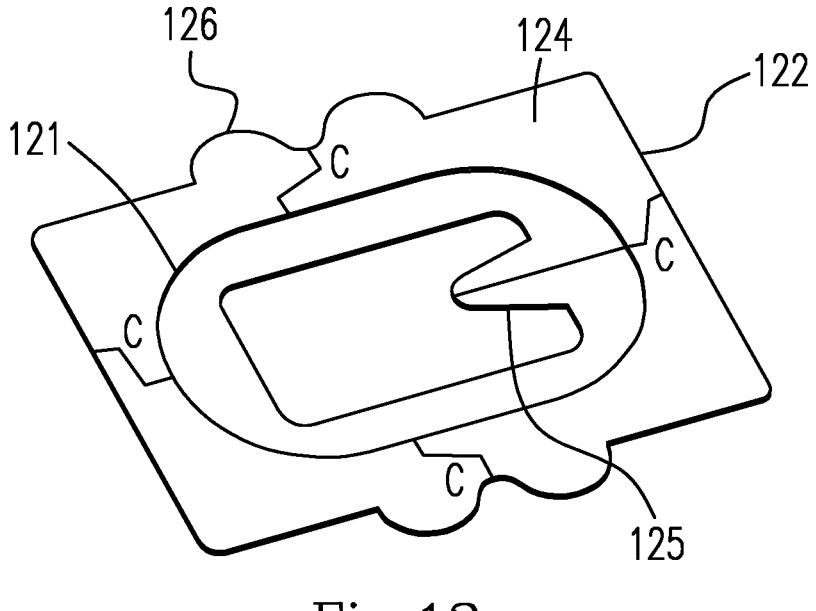
FIG. 12 shows a patch according to an embodiment of the present invention.
Figure 13:
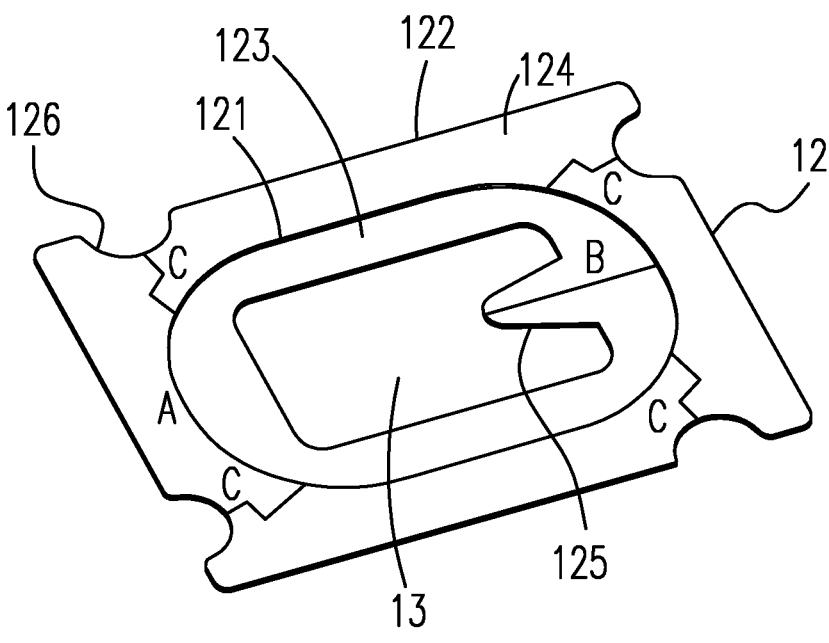
FIG. 13 shows a patch according to an embodiment of the present invention.

Please refer to FIGS. 5 and 7-8. After the inner peelable sheet 121 is peeled off, the outer peelable sheet 122 continuously provides the supporting force for the backing 111, and the backing 111 increases the strength of the physiological parameter detection device 21 attached to the skin surface.

Please refer to FIG. 1. The inner peelable sheet 121 and the outer peelable sheet 122 include at least one inner peelable sub-sheet 123 and at least one outer peelable sub-sheet 124, respectively.

Figure 14:
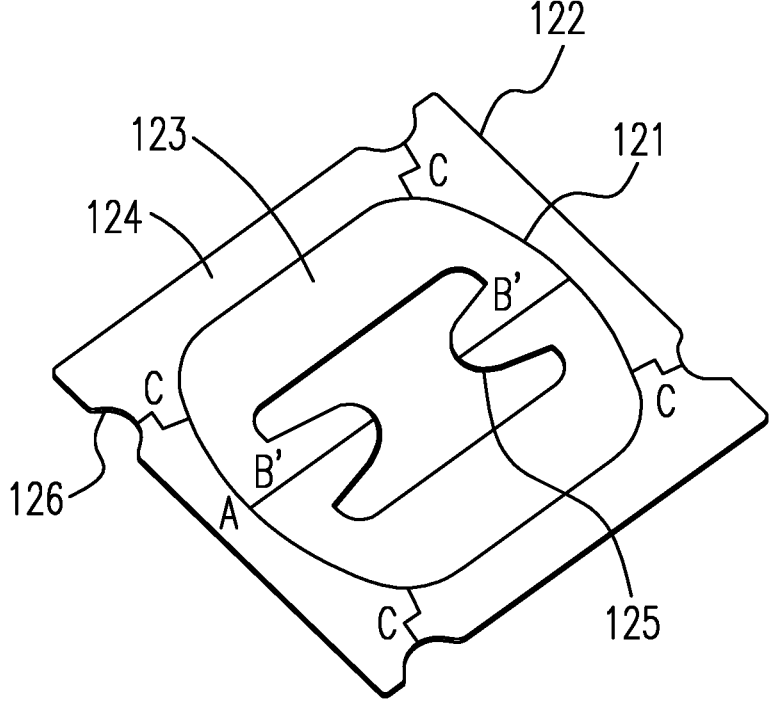
FIG. 14 shows a patch according to an embodiment of the present invention.
Figure 15:
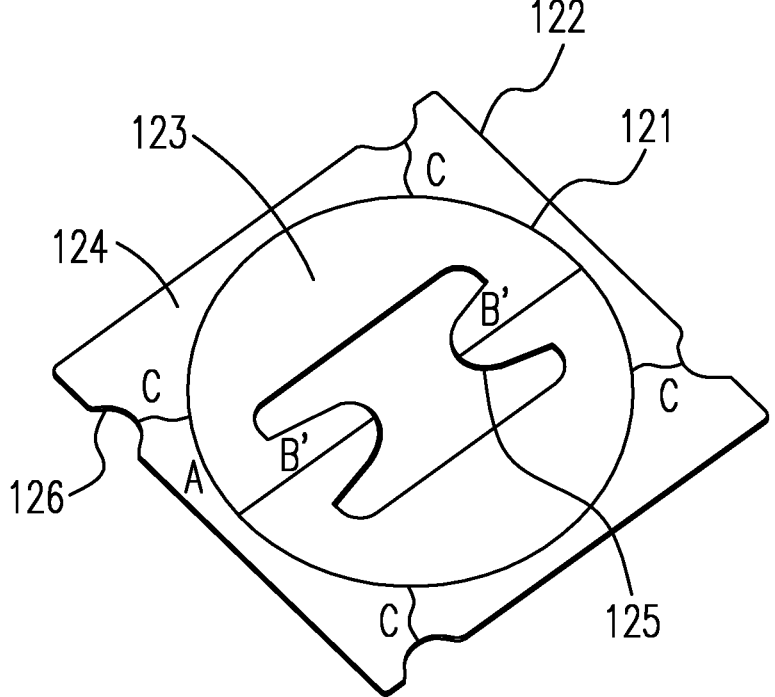
FIG. 15 shows a patch according to an embodiment of the present invention.

Please refer to FIGS. 1 and 14-15. In the patch system 1, a first cutting line A may be disposed between the inner peelable sheet 121 and the outer peelable sheet 122. When the number of the inner peelable sub-sheet 123 is one, a second cutting line B may be disposed on the inner peelable sub-sheet 123. When the inner peelable sheet 121 includes a plurality of the inner peelable sub-sheets 123, a second cutting line B' may be disposed between the inner peelable sub-sheets 123. At least one third cutting line C may be disposed between the outer peelable sub-sheets 124. The outer peelable sheet 122 may include, for example, four outer peelable sub-sheets 124.

Figure 2:
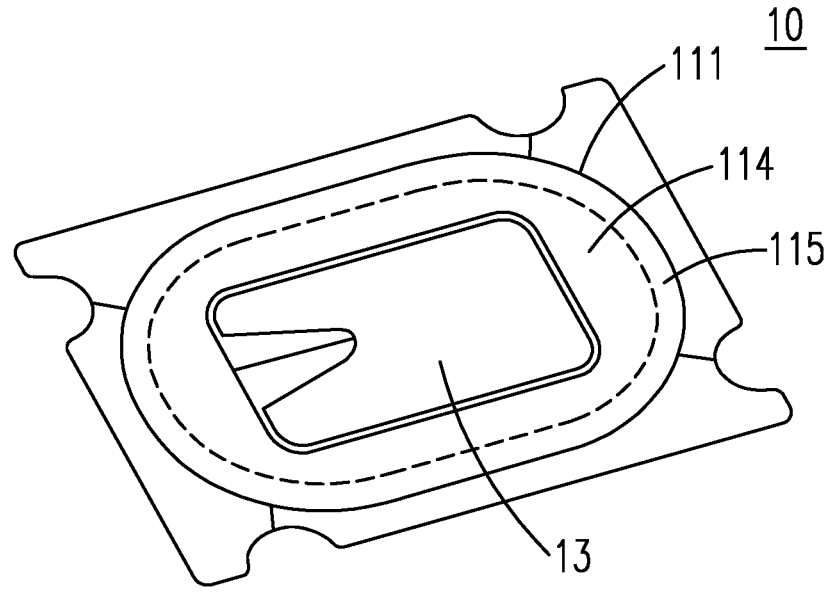
FIG. 2 shows a front view of the patch according to an embodiment of the present invention.
Figure 24A:
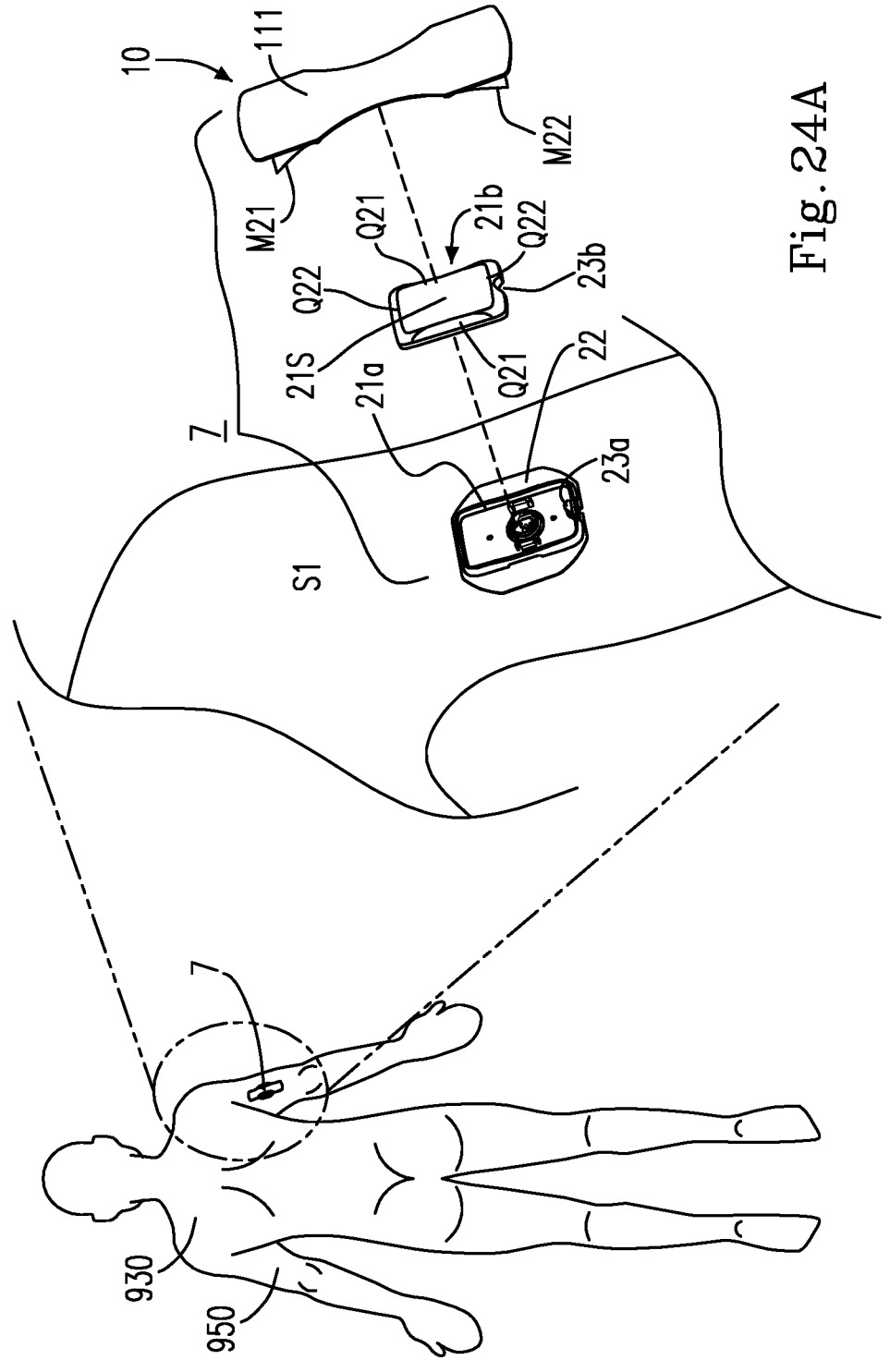
FIG. 24A, FIG. 24B, FIG. 24C, FIG. 24D, FIG. 24E and FIG. 24F respectively show an operation for the patch system using the patch of FIG. 23A and FIG. 23B.

Please refer to FIG. 2. In the patch system 1, the backing 111 have a shape of an ellipse. However, the backing 111 may have a shape of a rectangle or a circle. Alternatively, the backing 111 may be a strip and have a reduced width at its central region as shown in FIG. 24A. The present disclosure is not limited thereto.

In the patch system 1, the backing 111 may have a flexibility. The backing 111 may be a paper, a cloth, or a plastic mesh, and the peelable sheet 12 may be a release paper or a release sheet.

Please refer to FIGS. 1-2 and 7. In the patch system 1, the backing 111 may have a region 13, a first patch area 114 and a second patch area 115. The first patch area 114 and the second patch area 115 are extended from the surrounding of the region 13 so as to encompass the region 13. The first patch area 114 and the second patch area 115 correspond to the inner peelable sheet 121 and the outer peelable sheet 122 respectively. The region 13 has an area greater than that of the physiological parameter detection device 21 and less than that of the base patch 22 of the physiological parameter detection device 21. The inner peelable sheet 121 has an inner shorter than either side of that of the first patch area 114 to protect the adhesive surface 113 of the backing 111.

The region 13 may have a geometric shape. The region 13 may be a hole having a geometric shape.

Please refer to FIGS. 1 and 12-16. In the patch system 1, the inner peelable sheet 121 and the outer peelable sheet 122 may be respectively provided with at least one inner auxiliary tearing part 125 and at least one outer auxiliary tearing part 126, in which the outer auxiliary tearing part 126 may be protrusive or recessive.

Figure 16:
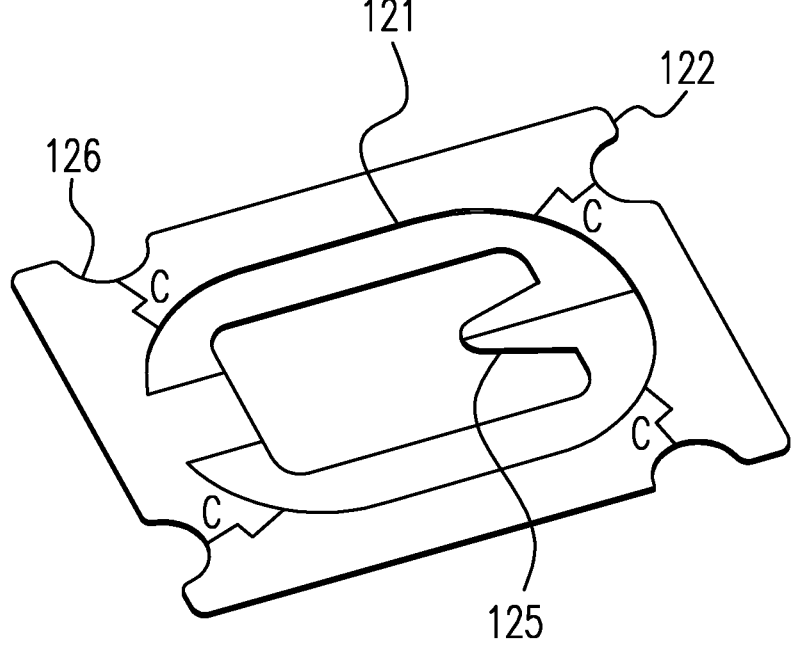
FIG. 16 shows a patch according to an embodiment of the present invention.

Please refer to FIGS. 1 and 16. In the patch system 1, the inner peelable sheet 121 may form a full circle or a non-full circle.

Please refer to FIGS. 1 and 12-16. The third cutting line C may be a curve, a polyline and a straight line. Compared with the straight line, when the third cutting line C is the curve or the polyline, the backing 111 can be kept flat and less likely to droop when the outer peelable sub-sheet 124 is peeled off.

Please refer to FIGS. 1-16. The second embodiment of the present invention provides a patch 10. The patch 10 includes a backing 111 and a peelable sheet 12. An adhesive layer 112 having an adhesive surface 113 is disposed on the backing 111. The backing 111 is adhered to a skin surface via the adhesive surface 113.

The peelable sheet 12 is detachably adhered to the adhesive surface 113. The peelable sheet 12 is used to preserve the adhesive surface 113 of the backing 111 and provide a supporting force to the backing 111. The peelable sheet 12 includes an inner peelable sheet 121 and an outer peelable sheet 122, wherein the both sheets are relatively easily peelable off from the adhesive surface 113. After the inner peelable sheet 121 is peeled off, the outer peelable sheet 122 continuously provides the supporting force for the backing 111 so as to perform a complete attaching of the backing 111 and allow the backing 111 to be adhered easily and evenly.

The backing 111 may have a region 13, a first patch area 114 and a second patch area 115. The first patch area 114 and the second patch area 115 are extended from the surrounding of the region 13. The first patch area 114 and the second patch area 115 correspond to the inner peelable sheet 121 and the outer peelable sheet 122 respectively. The region 13 has an area greater than that of a physiological parameter detection device 21 and less than that of a base patch 22 of the physiological parameter detection device 21.

The backing 111 and the peelable sheet 12 in the second embodiment of the present invention have the features as in the first embodiment of the present invention, and will not be described here.

Please refer to FIGS. 1-16. The third embodiment of the present invention provides a method for using the patch 10. The method includes the following steps.

Please refer to FIGS. 1-2. The patch 10 including the backing 111 and the peelable sheet 12 is provided. The backing 111 has the first patch area 114 and the second patch area 115. The peelable sheet 12 is attached to the first patch area 114 and the second patch area 115 for providing the supporting force to the backing 111, and includes an inner peelable sheet 121 and an outer peelable sheet 122, in which the both sheets are relatively easily peelable off. The inner peelable sheet 121 and the outer peelable sheet 122 include at least one inner peelable sub-sheet 123 and at least one outer peelable sub-sheet 124, respectively.

Please refer to FIG. 7. The physiological parameter detection device 21 having the base patch 22 is provided. The physiological parameter detection device 21 is adhered to the skin surface of the user via the base patch 22.

Figure 4:
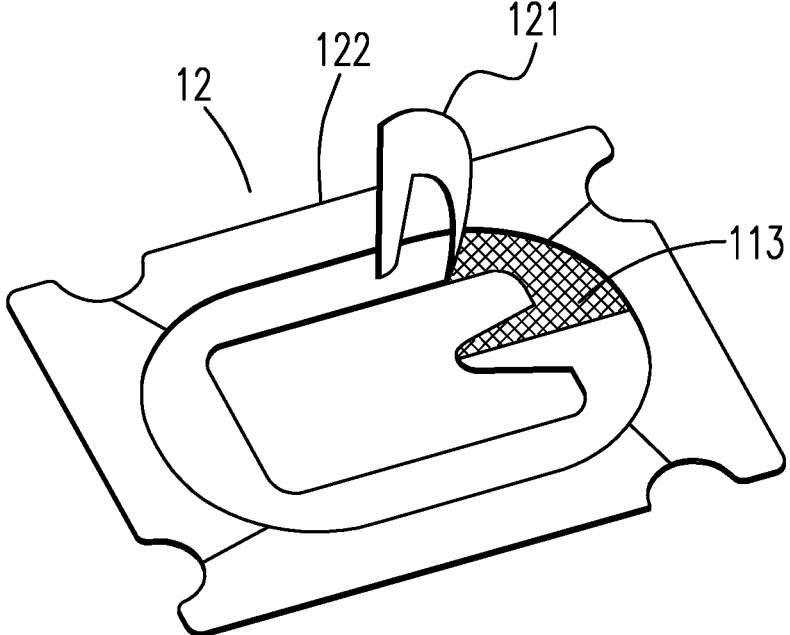
FIG. 4 shows a use state of the patch according to an embodiment of the present invention.

Please refer to FIGS. 4-5. The inner peelable sheet 121 is peeled off to expose a surface of the first patch area 114 corresponding to the inner peelable sheet 121.

Please refer to FIGS. 5 and 7-8. After the inner peelable sheet 121 is peeled off, the outer peelable sheet 122 continuously provides the supporting force for the backing 111 so as to perform a complete attaching of the backing 111 and allow the backing 111 to be adhered easily and evenly.

Please refer to FIGS. 6 and 9-11. The outer peelable sheet 122 is peeled off to expose a surface of the second patch area 115 corresponding to the outer peelable sheet 122. Thereby, the adhesive strength of the physiological parameter detection device 21 on the skin surface is enhanced through the backing 111.

Figure 17:
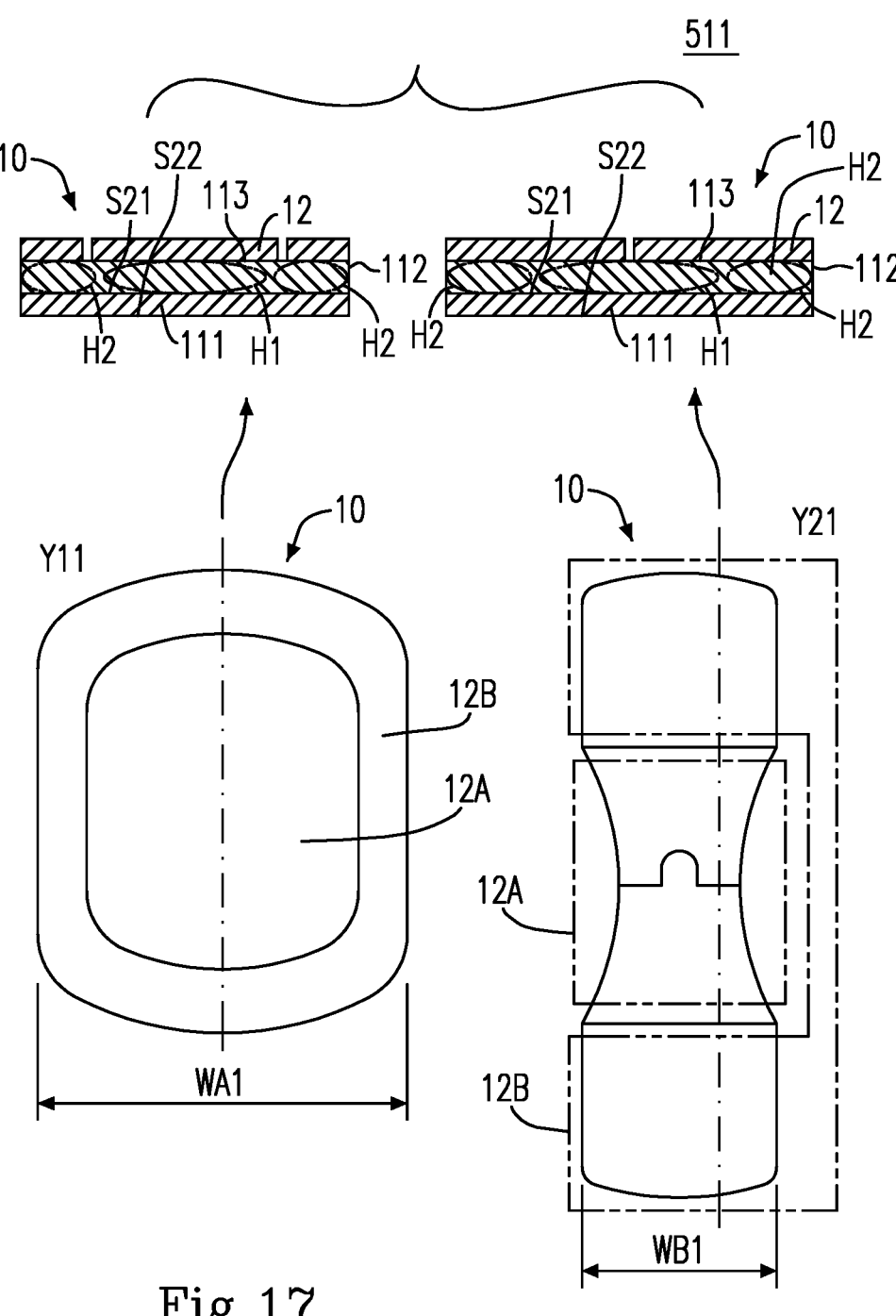
FIG. 17 shows a patch according to an embodiment of the present invention.

Please refer to FIG. 17, which shows an implementation structure 511 of the patch 10 in the present disclosure. As shown in FIG. 17, the patch 10 includes a backing 111, an adhesive layer 112 and a peelable sheet 12. The backing 111 has a backing surface S21 and a backing surface S22 being opposite to the backing surface S21. The adhesive layer 112 is disposed on one (such as the backing surface S21) of the backing surfaces S21 and S22 for forming an adhesive surface 113 thereon. The adhesive surface 113 includes a central adhesive portion H1 and at least one outer adhesive portion H2. The peelable sheet 12 of the patch 10 is detachably adhered to the adhesive layer 112 for preserving the adhesive surface 113, and provides a supporting (stretching-up) force for the backing 111. The peelable sheet 12 includes an inner peelable portion 12A and an outer peelable portion 12B, respectively, corresponding to the central adhesive portion H1 and the outer adhesive portion H2. The patch 10 of the present disclosure can be summarized to be in one of a structural state Y11 and a structural state Y21. The patch 10 being in the structural state Y11 has a width WA1. The patch 10 being in the structural state Y21 has a width WB1. In particular, the width WA1 is greater than a width of the physiological parameter detection device (not shown in the figure), and the width WB1 is not greater than the width of the physiological parameter detection device. The central adhesive portion H1 is surrounded by the outer adhesive portion H2 in the structural state Y11. In the structural state Y21, the outer adhesive portion H2 is separated by the central adhesive portion H1 so as to be disposed at the two opposite sides of the central adhesive portion H1.

Figure 18:
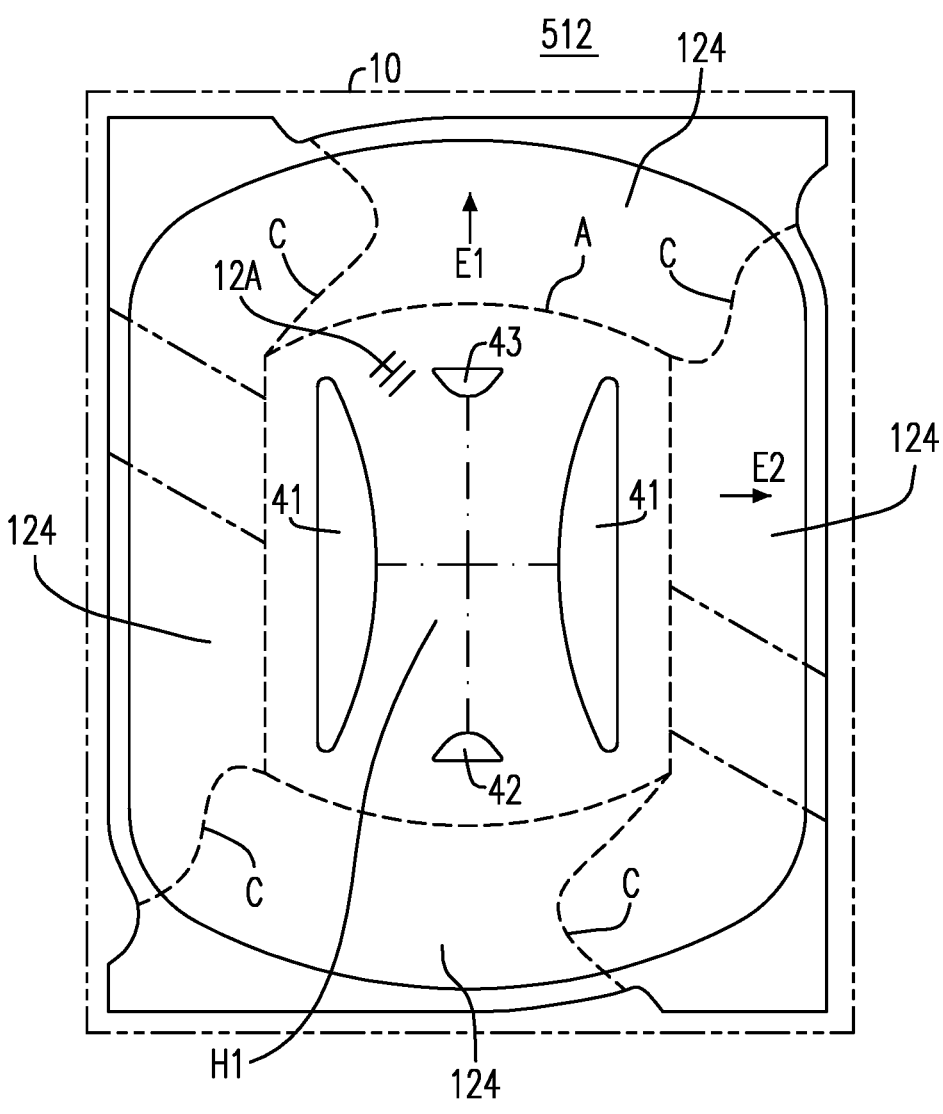
FIG. 18 shows an implementation structure of the patch in FIG. 17.
Figure 19A:
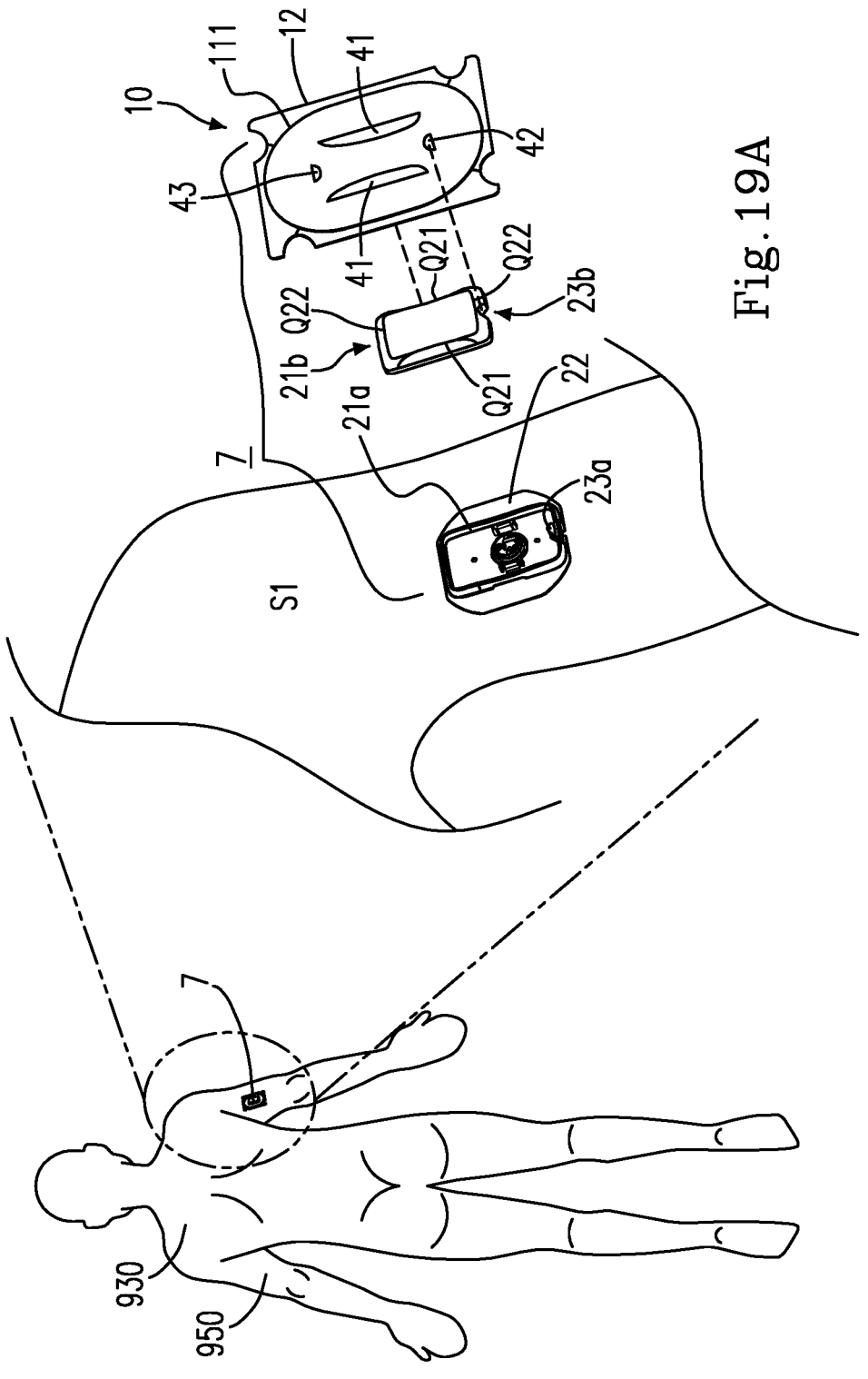
FIG. 19A and FIG. 19B respectively show a patch system using the patch of FIG. 18.
Figure 19B:
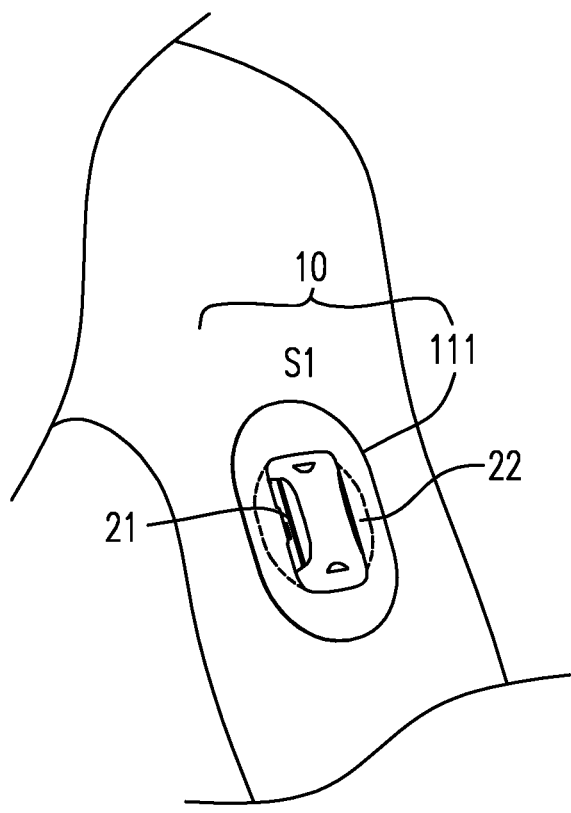
Figures 20A, 20B:
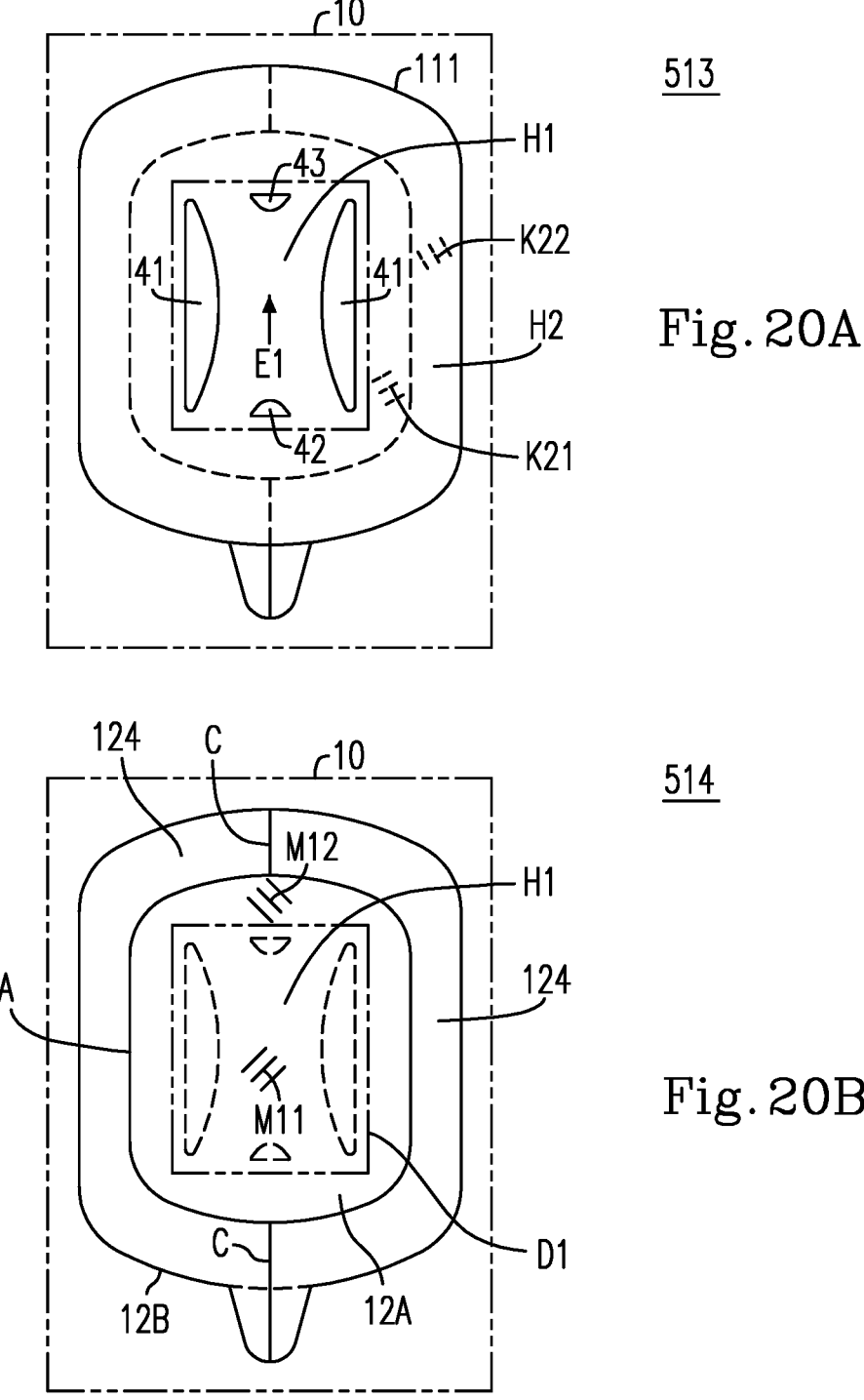
FIG. 20A, FIG. 20B and FIG. 21 respectively show a plurality of implementation structures of the patch shown in FIG. 17.
Figure 21:
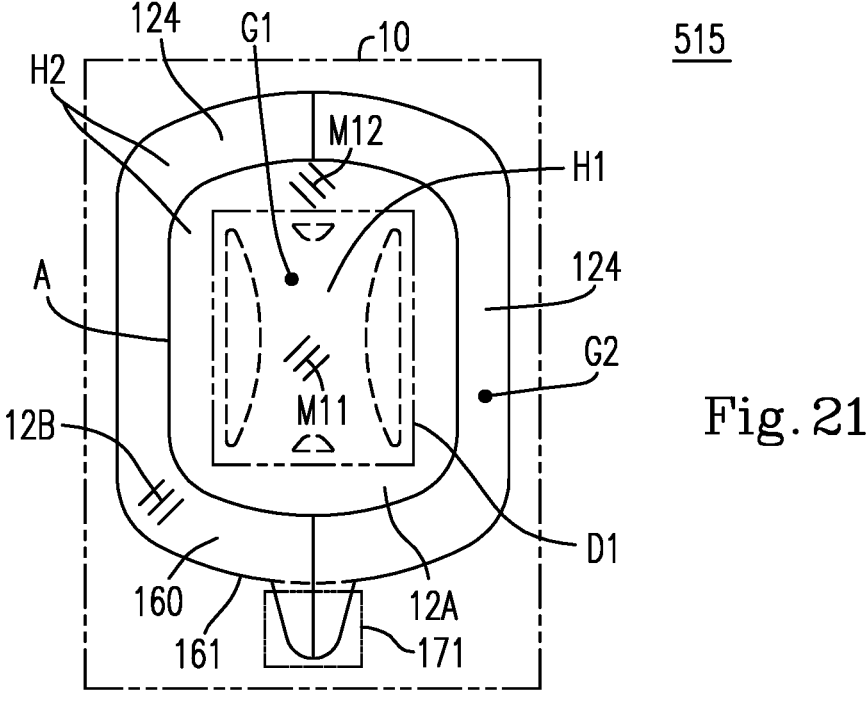
Figure 22:
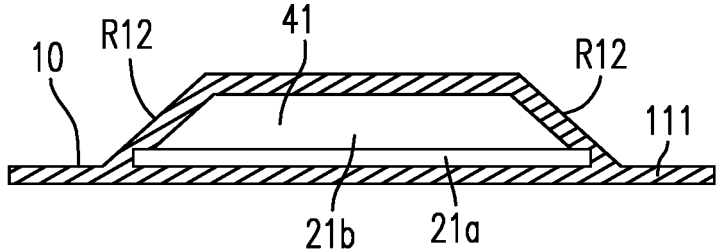
FIG. 22 is a side view showing the patch system of FIG. 19B.

Please refer to FIG. 18, FIG. 19A, FIG. 19B, FIG. 20A, FIG. 20B, FIG. 21 and FIG. 22. FIGS. 18, FIG. 20A, FIG. 20B and FIG. 21 respectively show a plurality of implementation structures 512, 513, 514 and 515 of the patch 10 shown in FIG. 17. Each of FIGS. 18, 20A, 20B and 21 is associated with the structural state Y11. FIG. 20A is a front view, that is viewed in a direction from the backing 111 to the peelable sheet 12, of the patch 10. FIG. 20B and FIG. 21 are rear view, which are viewed in a direction from the peelable sheet 12 to the backing 111, of the patch 10. FIG. 19A, FIG. 19B and FIG. 22 show a patch system 7 using the patch 10 of FIG. 18, in which FIG. 19A shows an exploded view of the patch system 7, FIG. 19B shows an assembly state of the patch system 7, and FIG. 22 shows a side view for the assembly state of the patch system 7.

As shown in FIGS. 19A and 19B, the patch system 7 includes a base patch 22, a patch 10, and a physiological parameter detection device 21 disposed between the base patch 22 and the patch 10. The physiological parameter detection device 21 includes a base 21a and a transmitter 21b. The transmitter 21b is to be installed to the base 21a, and is detachable. The physiological parameter detection device 21 can be adhered to a skin surface S1 of a human body 930 with the base patch 22. As shown in FIG. 19B, the adhesion strength of the physiological parameter detection device 21 on the skin surface S1 can be improved through the patch 10 . . . . Thus, the patch 10 is a reinforcement patch 10, and is used by a user 950. For example, the user 950 has the human body 930.

When the inner peelable portion 12A is removed to expose the central adhesive portion H1 and the patch 10 is caused to apply a pressure P1 to the transmitter 21b of the physiological parameter detection device 21, the central adhesive portion H1 is adhered to the top surface 21S of the transmitter 21b of the physiological parameter detection device 21 and the outer peelable portion 12B, which is not peeled off, continuously provides the supporting force for the backing 111 so as to avoid the patch 10 from bunching up and getting wrinkled. Afterward, the outer peelable portion 12B can be sequentially peeled off to cause the outer adhesive portion H2 to be adhered onto the physiological parameter detection device 21, the base patch 22 and the skin surface S1 as shown in FIG. 19B.

As shown in FIGS. 18-19B, the patch 10 includes the adhesive layer 112. The skin surface S1 is a skin surface of the human body 930. The patch 10 further includes at least one hole 41 passing through the backing 111. The hole 41 is located in the central adhesive portion H1, or is located between the central adhesive portion H1 and the outer adhesive portion H2. When the patch 10 is caused to apply the pressure P1 to the physiological parameter detection device 21, the hole 41 is preferably configured to correspond to at least one long side Q21 of the transmitter 21b. That is, when the central adhesive portion H1 of the patch 10 is prepared to be adhered to the top surface 21S of the transmitter 21b, a position alignment can be performed in advance through the hole 41 and the long side Q21 of the transmitter 21b. Thereby, an unexpected displacement can be avoided. In addition, the backing 111 has a longitudinal direction E1 and a specific direction E2 being perpendicular to the longitudinal direction E1. In one embodiment, a ductility of the backing 111 in the longitudinal direction E1 is larger than a ductility of the backing 111 in the specific direction E2. The central adhesive portion H1 is disposed along the longitudinal direction E1, and preferably, the hole 41 is also disposed along the longitudinal direction E1. Moreover, the adhesion area is too large to cause a residual adhesive necessary to be cleaned when the physiological parameter detection device 21 is used repetitively. Accordingly, an adhesive force per unit area G1 of the central adhesive portion H1 can be less than an adhesive force per unit area G2 of the outer adhesive portion H2.

In FIG. 19B, the transmitter 21b of the physiological parameter detection device 21 can further include at least one fool-proof surface structure 23b. The base 21a of the physiological parameter detection device 21 can be disposed with another fool-proof surface structure 23a corresponding to the fool-proof surface structure 23b. When the transmitter 21b is prepared to be disposed to the base 21a, a position alignment can be performed in advance by aligning the fool-proof surface structure 23b of the transmitter 21b with the fool-proof surface structure 23a of the base 21a. The transmitter 21b is then pressed downwardly to complete the installation. Accordingly, the backing 111 can further include another hole 42. The hole 42 is configured to be aligned to the fool-proof surface structure 23b of the transmitter 21b so as to strengthen the accuracy of the alignment during the adhesion of the patch 10. More particularly, the backing 111 can include further another hole 43. When the patch 10 is caused to apply the pressure P1 toward the physiological parameter detection device 21, the hole 43 is configured to correspond to at least one short side Q22 of the transmitter 21b.

As shown in FIGS. 18-21, the outer adhesive portion H2 extending from the central adhesive portion H1 is disposed to surround the central adhesive portion H1. The inner peelable portion 12A and the outer peelable portion 12B have a first cutting line A therebetween. The outer peelable portion 12B has at least one third cutting line C to include a plurality of outer peelable sub-sheets 124 so that the user 950 can peel the outer peelable sub-sheets 124 in stages for maintaining the flatness of the backing 111 during the adhesion. In the implementation structure 512 of FIG. 18, the quantity of the outer peelable sub-sheets 124 is four so as to allow each of the outer peelable sub-sheets 124 to be peeled along a straight line.

In addition, the implementation structures 513, 514 and 515 respectively shown in FIG. 20A, FIG. 20B and FIG. 21 are similar to the implementation structure 512 of FIG. 18. The profiles of the peelable sheet 12 and the backing 111 are substantially the same, and other features of the patch 10 will be described as follows. The outer adhesive portion H2 includes a first patch area K21 and a second patch area K22. The inner peelable portion 12A of the peelable sheet 12 corresponds to a combination of the central adhesive portion H1 and the first patch area K21. The outer peelable portion 12B of the peelable sheet 12 corresponds to the second patch area K22.

The inner peelable portion 12A includes a first inner peelable sub-portion M11 and a second inner peelable sub-portion M12 respectively corresponding to the central adhesive portion H1 and the first patch area K21. The first and the second inner peelable sub-portion M11 and M12 have a fourth cutting line D1 therebetween. After the first inner peelable sub-portion M11 is peeled off, the second inner peelable sub-portion M12 and the outer peelable portion 12B can continuously provide the supporting force for the backing 111 so as to allow the central adhesive portion H1 to be easily adhered to the top surface 21S of the transmitter 21b of the physiological parameter detection device 21. In this embodiment, the adhesive surface 113 will not be exposed too much at one time for protection. In the meanwhile, the flatness of the backing 111 can be maintained. However, the fourth cutting line D1 can be omitted as shown in the implementation structure 512 of FIG. 18. Alternatively, an area of the inner peelable portion 12A can adjusted to only protect the central adhesive portion H1. The present disclosure is not limited thereto.

In the implementation structures 513, 514 and 515, the quantity of the outer peelable sub-sheets 124 can be two.

Referring to FIG. 21, the outer peelable portion 12B includes a main body portion 160 and at least one auxiliary peeling part 171 extending from the main body portion 160. The shape of the auxiliary peeling part 171 may be, but not limited to, a protrusion shape, and is protruded outward from an outer edge 161 of the main body portion 160. The auxiliary peeling part 171 is held by the user 950, and is used to peel off the outer peelable portion 12B.

Similarly, cooperated with FIG. 19A, when the inner peelable portion 12A is removed to expose the central adhesive portion H1 and the patch 10 is caused to downward press the physiological parameter detection device 21 by using the adhesive surface 113, the central adhesive portion H1 is adhered to the top surface 21S of the transmitter 21b of the physiological parameter detection device 21. At this time, the second inner peelable sub-portion M12 and the outer peelable portion 12B continuously provide the supporting force for the backing 111 so as to maintain the flatness of the backing 111 of the patch 10. Afterward, the second inner peelable sub-portion M12 is peeled off to allow the first patch area K21 of the outer adhesive portion H2 to be adhered to the physiological parameter detection device 21, the base patch 22 and even the skin surface S1. Finally, the plurality of outer peelable sub-sheets 124 are sequentially peeled off to allow the second patch area K22 of the outer adhesive portion H2 to be adhered to the skin surface S1.

Referring to FIG. 22, under a condition that the patch 10 is adhered onto the physiological parameter detection device 21 and the skin surface S1, the patch 10 provides a downward pressure P1 to the physiological parameter detection device 21, wherein the pressure P1 is used to enhance an adhesion strength of the physiological parameter detection device 21 to the skin surface S1. The physiological parameter detection device 21 has the top surface 21S, long sides Q21 and short sides Q22. The patch 10 provided in the present invention can provide the downward pressure P1 to enhance the adhesion strength of the physiological parameter detection device 21 to the skin surface S1; in addition, the central region of the patch 10 has a specific designed shape, and is adhered along the top surface 21S and the short sides Q22 to form an inclined surface. When a garment is worn or is taken off, the garment is slid along the inclined surface formed by the patch 10, so that it is avoided that the physiological parameter detection device 21 is dropped in the course that the garment is worn or is taken off. Preferably, the inclined surface formed by using the top surface 21S and the short sides Q22 is a continuous surface.

Figures 23A, 23B:
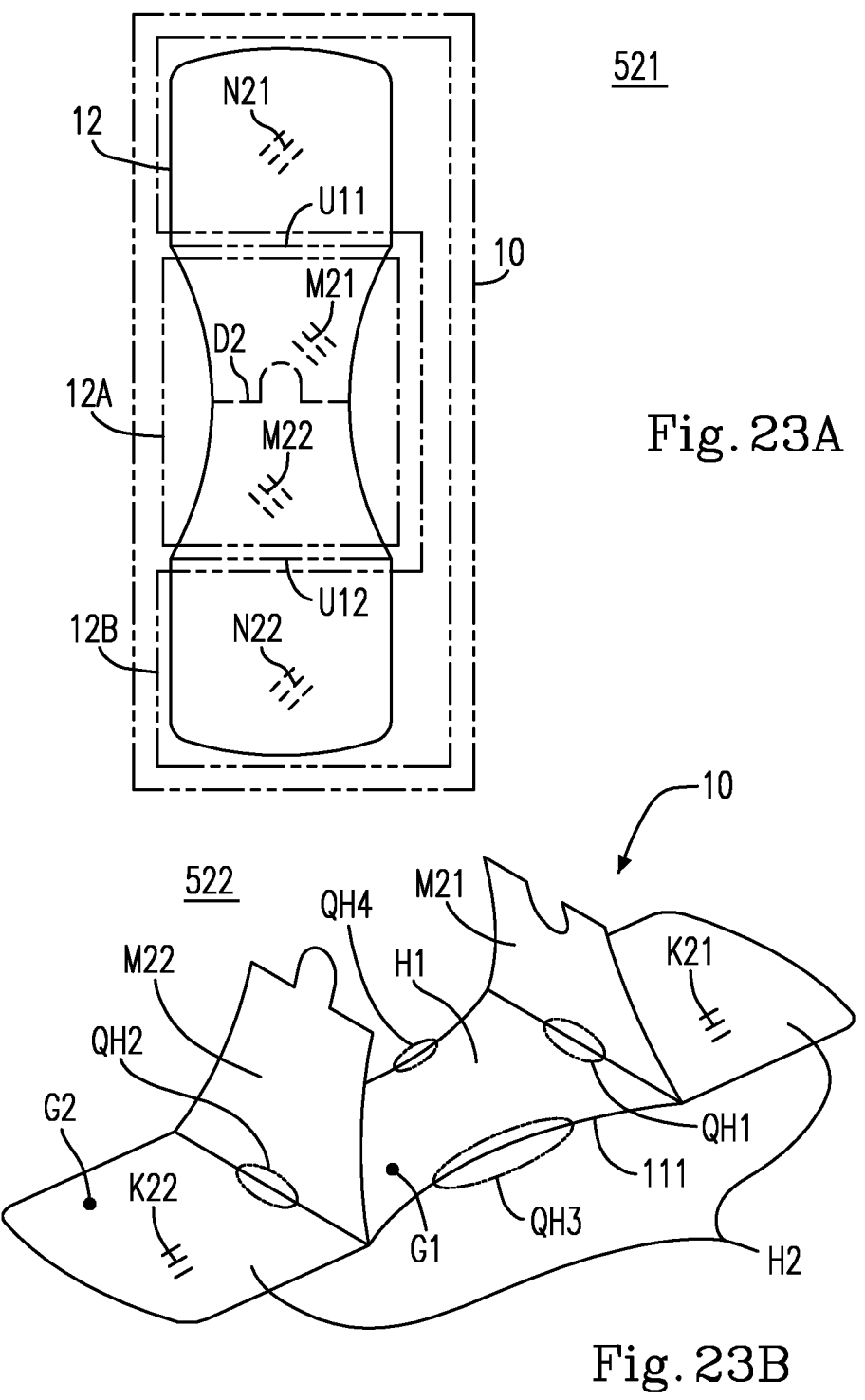
FIG. 23A and FIG. 23B respectively show another two implementation structures of the patch shown in FIG. 17.
Figures 24B, 24C:
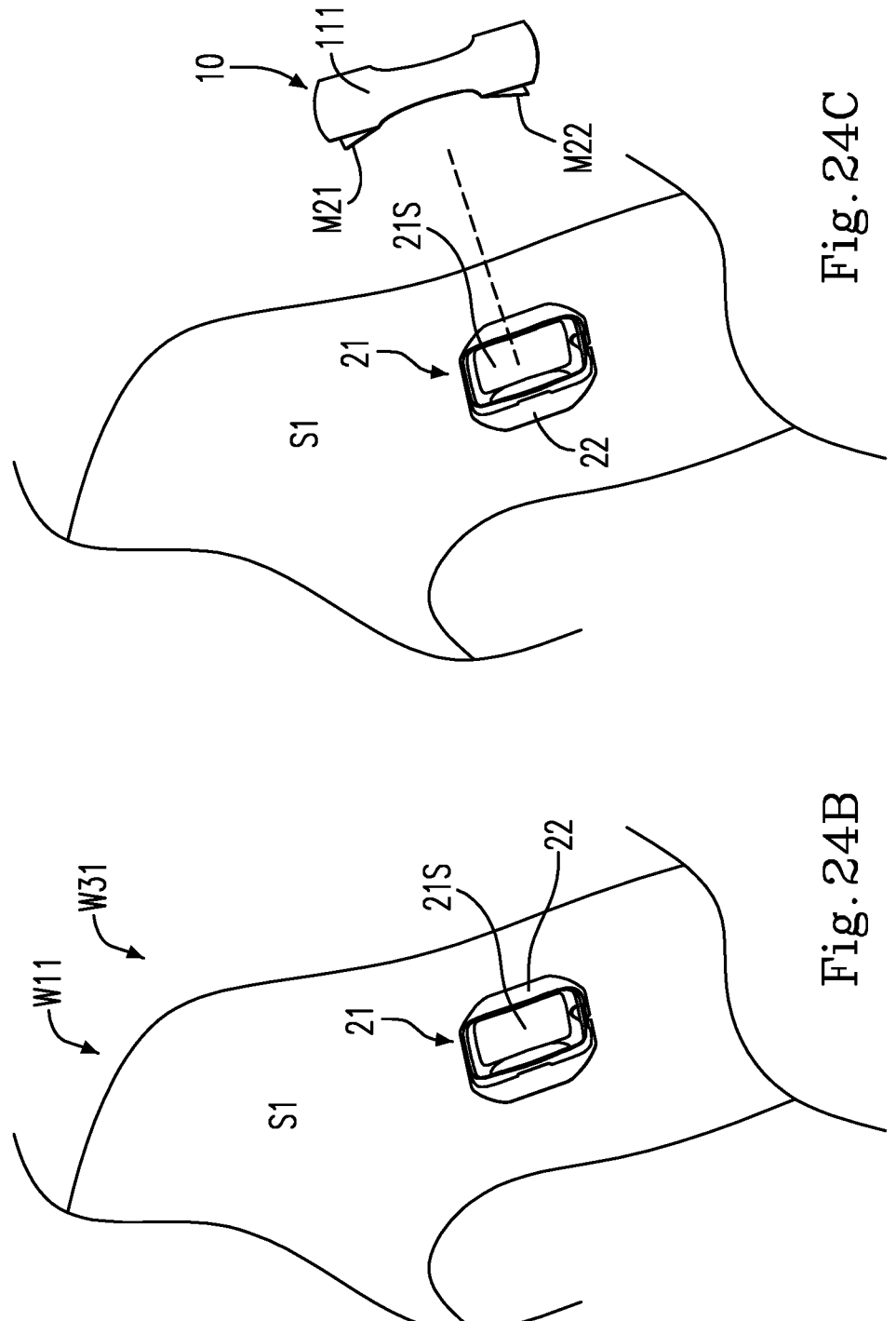

Please refer to FIG. 23A, FIG. 23B, FIG. 24A, FIG. 24B, FIG. 24C, FIG. 24D, FIG. 24E and FIG. 24F. FIGS. 24A and 24B respectively show two implementation structures 521 and 522 of the patch 10 shown in FIG. 17, and both of them are associated with the structural state Y21. FIGS. 24A, 24B, 24C, 24D, 24E and 24F respectively show the patch system 7 using the patch 10 of FIG. 23A and FIG. 23B, in which FIG. 24A is a schematic diagram showing an explode state of the patch system 7, and FIGS. 24B-24F show an operation of the patch system 7.

As shown in FIGS. 23A and 23B, the outer adhesive portion H2 is symmetrically disposed on two sides of the central adhesive portion H1, and includes a first patch area K21 and a second patch area K22. The outer peelable portion 12B has two outer peelable sub-portions N21 and N22 respectively corresponding to the first and the second patch areas K21 and K22.

The inner peelable portion 12A corresponds to the central adhesive portion H1, and includes a first inner peelable sub-portion M21 and a second inner peelable sub-portion M22 which are separate mutually. Under a condition that the first and the second inner peelable sub-portion M21 and M22 are lifted and the lifted first and the second inner peelable sub-portion M21 and M22 are respectively folded toward the two outer peelable sub-portions N21 and N22 to expose the central adhesive portion H1, the two outer peelable sub-portions N21 and N22 can continuously provide the supporting force for the backing 111 so as to maintain the flatness of the backing 111 of the patch 10. The first and the second inner peelable sub-portion M21 and M22 of the inner peelable portion 12A are mutually separate by a fourth cutting line D2. The fourth cutting line D2 can be a curve, a polyline or a straight line.

In some embodiments, although it is not shown in the figure, the inner peelable portion 12A can be a single piece and cover the central adhesive portion H1. At this time, at least one of the two sides QH1 and QH2 of the inner peelable portion 12A is separate from at least one of the two outer peelable sub-portions N21 and N22. For example, the side QH1 of the inner peelable portion 12A is separated from the outer peelable sub-portions N21. When the inner peelable portion 12A is lifted to expose the central adhesive portion H1, the two outer peelable sub-portions N21 and N22 can continuously provide the supporting force for the backing 111 so as to maintain the flatness of the backing 111 of the patch 10.

Backward to FIG. 23A, the inner peelable portion 12A is connected to the outer peelable portion 12B through at least one pre-pressing line U11. The inner peelable portion 12A can be lifted and is folded toward the outer peelable portion 12B with respect to the pre-pressing line U11 so as to expose the central adhesive portion H1. Preferably, the pre-pressing line U11 is a continuous pre-pressing line, or is a non-continuous pre-pressing line. It is noted that the pre-pressing line U11 cannot be only applied to the structural state Y21 of FIG. 17 but also the structural state Y11. For example, the pre-pressing line can be disposed on the outer peelable sheet 124 for ensuring the flatness of the backing 111 during the peeling procedure of the outer peelable sheet 124.

In conjunction with FIG. 24A, the central adhesive portion H1 has a plurality of sides QH1, QH2, QH3 and QH4. As mentioned above, the transmitter 21b of the physiological parameter detection device 21 has two long sides Q21 and two short sides Q22. The central adhesive portion H1 is disposed to cause the two sides QH3 and QH4 of the central adhesive portion H1 to correspond, respectively, to the two long sides Q21 of the transmitter 21b of the physiological parameter detection device 21, thereby performing a position alignment.

The patch 10 is adhered to the physiological parameter detection device 21 with an adhesion area. Preferably, an adhesive force per unit area G1 of the central adhesive portion H1 is less than an adhesive force per unit area G2 of the outer adhesive portion H2, so that a problem of the adhesion area is avoided. The problem is that the adhesion area is too large to cause a residual adhesive necessary to be cleaned when the transmitter 21b of the physiological parameter detection device 21 is used repetitively.

Please refer to FIGS. 24A-24F. The physiological parameter detection device 21 shown in FIG. 24A includes a base patch 22, a base 21a and a transmitter 21b. As shown in FIG. 24B, the base 21a is adhered onto the skin surface S1 with the base patch 22. The transmitter 21b is installed to the base 21a.

Figures 24D, 24E:
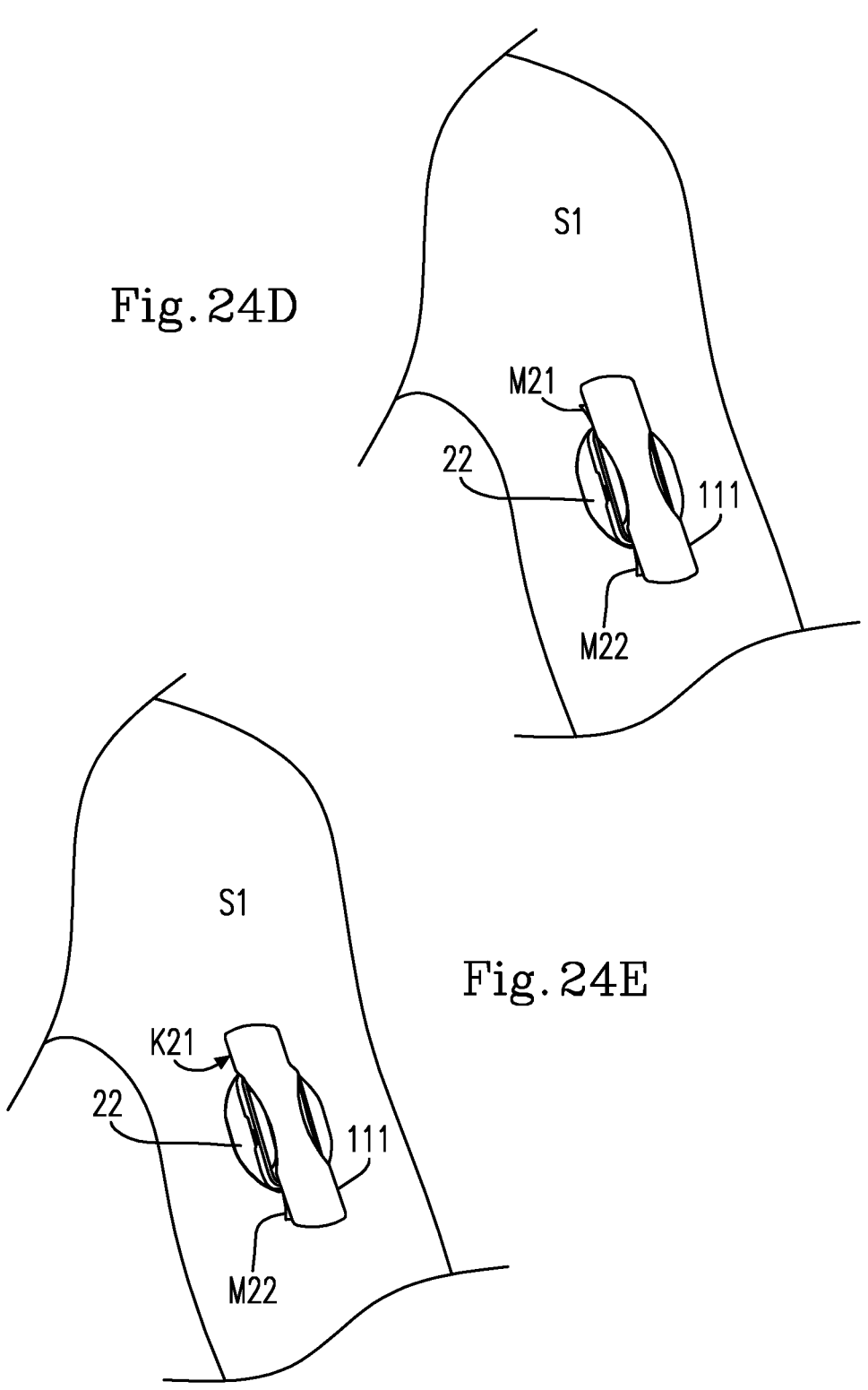

As shown in FIG. 24C, in conjunction with FIG. 23B, the central adhesive portion H1 is ready to be adhered onto the top surface 21S of the transmitter 21b. As shown in FIG. 24D, the central adhesive portion H1 is adhered onto the top surface 21S of the transmitter 21b. In FIG. 24D, the inner peelable portion 12A has not been peeled off yet so as to continuously support the backing 111; and the backing 111 has not been adhered to the skin surface S1 by downward pressing.

As shown in FIG. 24E, the outer peelable sub-portions N21 is peeled off by using the first inner peelable sub-portion M21, which is lifted, as an auxiliary peeling part. Then, the first patch area K21 of the backing 111 is downward pressed to be adhered to the side Q22 of the transmitter 21b, the base 21a and the skin surface S1. Depended on the area of the base patch 22, the patch 10 has possibility to be adhered to a portion of the base patch 22.

Figure 24F:
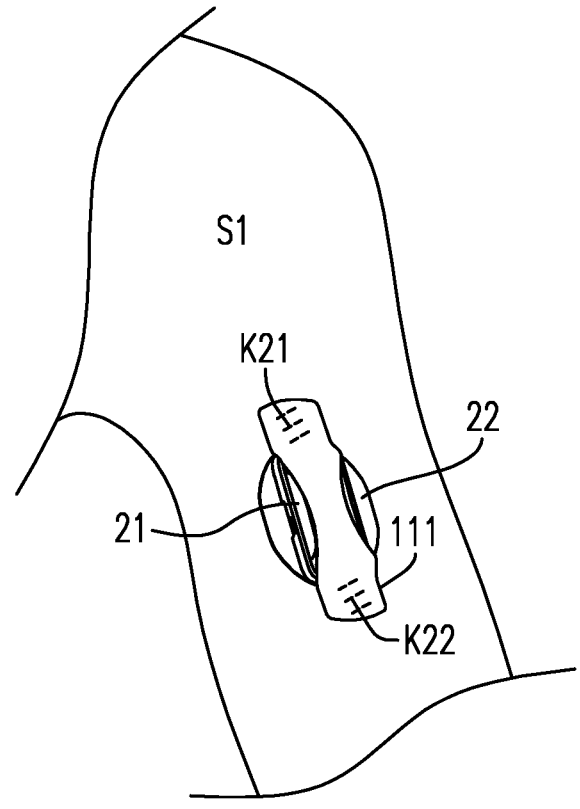

As shown in FIG. 24F, the outer peelable sub-portions N22 is peeled off by using the second inner peelable sub-portion M22, which is lifted, as an auxiliary peeling part. Then, the second patch area K22 of the backing 111 is downward pressed to be adhered to the side Q22 of the transmitter 21b, the base 21a and the skin surface S1. Thus, the backing 111 is finished to be adhered to the physiological parameter detection device 21 and the skin surface S1.

A method W11 (or an installation method) for adhering the patch 10 to the physiological parameter detection device 21 is disclosed. The method W11 includes the following steps: A physiological parameter detection device 21 is provided, wherein the physiological parameter detection device 21 at least includes a base 21a and a transmitter 21b, the base 21a is disposed on the skin surface S1 with a base patch 22, and the transmitter 21b is detachably installed to the base 21a and has a top surface 21S. In addition, after the base 21a is adhered to the skin surface S1 with the patch 22, the transmitter 21b is installed to the base 21a.

The method W11 further includes the following steps: The first and the second inner peelable sub-portions M21 and M22 of the patch 10 are lifted with respect to the cutting line D2 to expose the central adhesive portion H1. The patch 10 is caused to be downward press the physiological parameter detection device 21 by using the exposed central adhesive portion H1 so as to cause the exposed central adhesive portion H1 to be adhered to the top surface 21S of the transmitter 21b. In addition, the two outer peelable sub-portions N21 and N22 are peeled off by taking the first and the second inner peelable sub-portions M21 and M22 as force application points so as to allow the outer adhesive portion H2 to be adhered onto the physiological parameter detection device 21 and the skin surface S1.

Figure 25A:
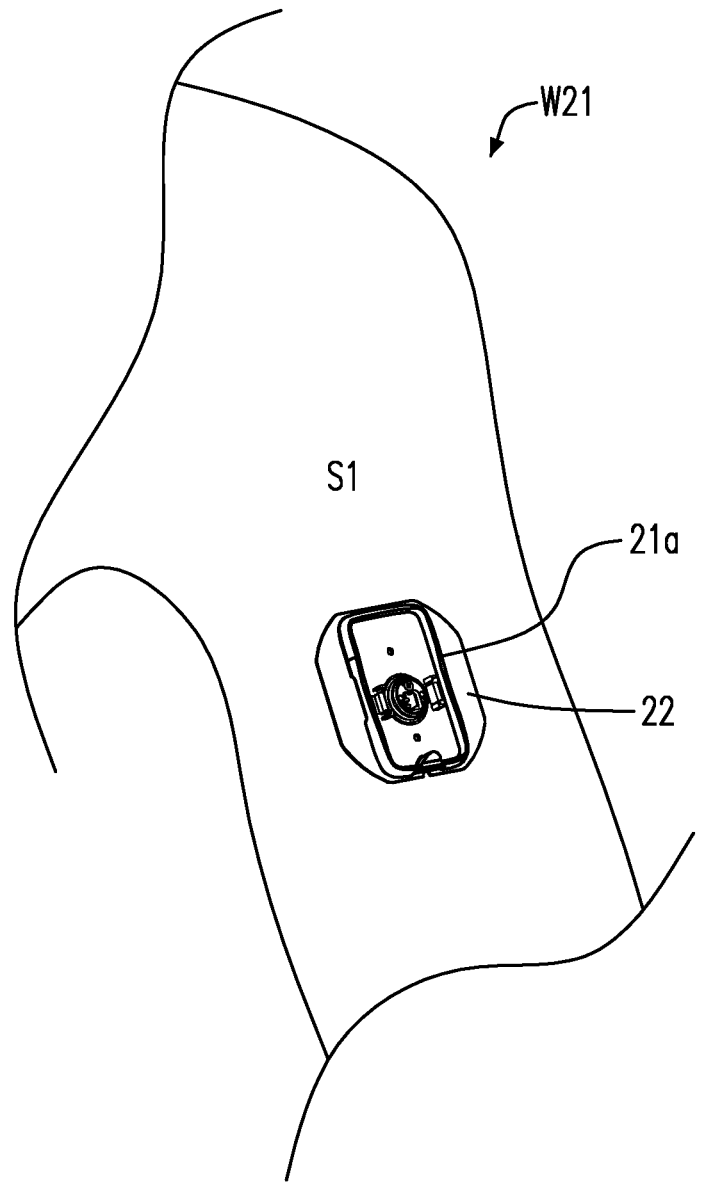
FIG. 25A, FIG. 25B, FIG. 25C, FIG. 25D, FIG. 25E, FIG. 25F and FIG. 25G respectively show another operation for the patch system using the patch of FIG. 23A and FIG. 23B.
Figures 25B, 25C:
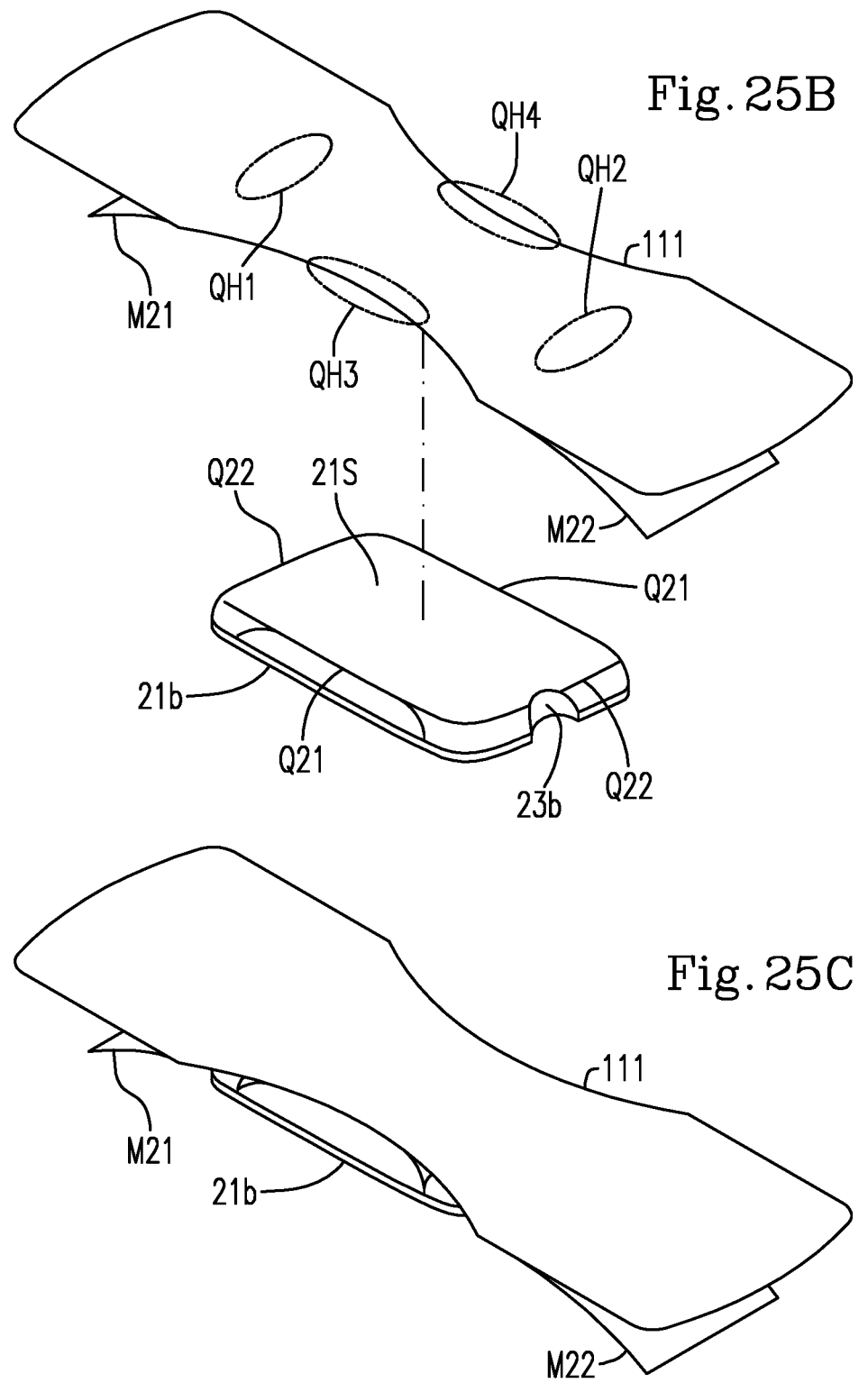

Please refer to FIG. 25A, FIG. 25B, FIG. 25C, FIG. 25D, FIG. 25E, FIG. 25F and FIG. 25G, which respectively show the patch system 7 using the above-mentioned patch 10. As shown in FIG. 25A, the base 21a is adhered onto the skin surface S1 with the base patch 22. As shown in FIG. 25B, the transmitter 21b is separate from the base 21a; and the central adhesive portion H1 is ready to be adhered onto the top surface 21S of the transmitter 21b. In Particular, the backing 111 can utilize the sides QH3 and QH4 of its central adhesive portion H1 to perform a position alignment with the two long sides Q21 of the transmitter 21b. Then, the central adhesive portion H1 is adhered onto the top surface 21S of the transmitter 21b as shown in FIG. 25C.

Figure 25D:
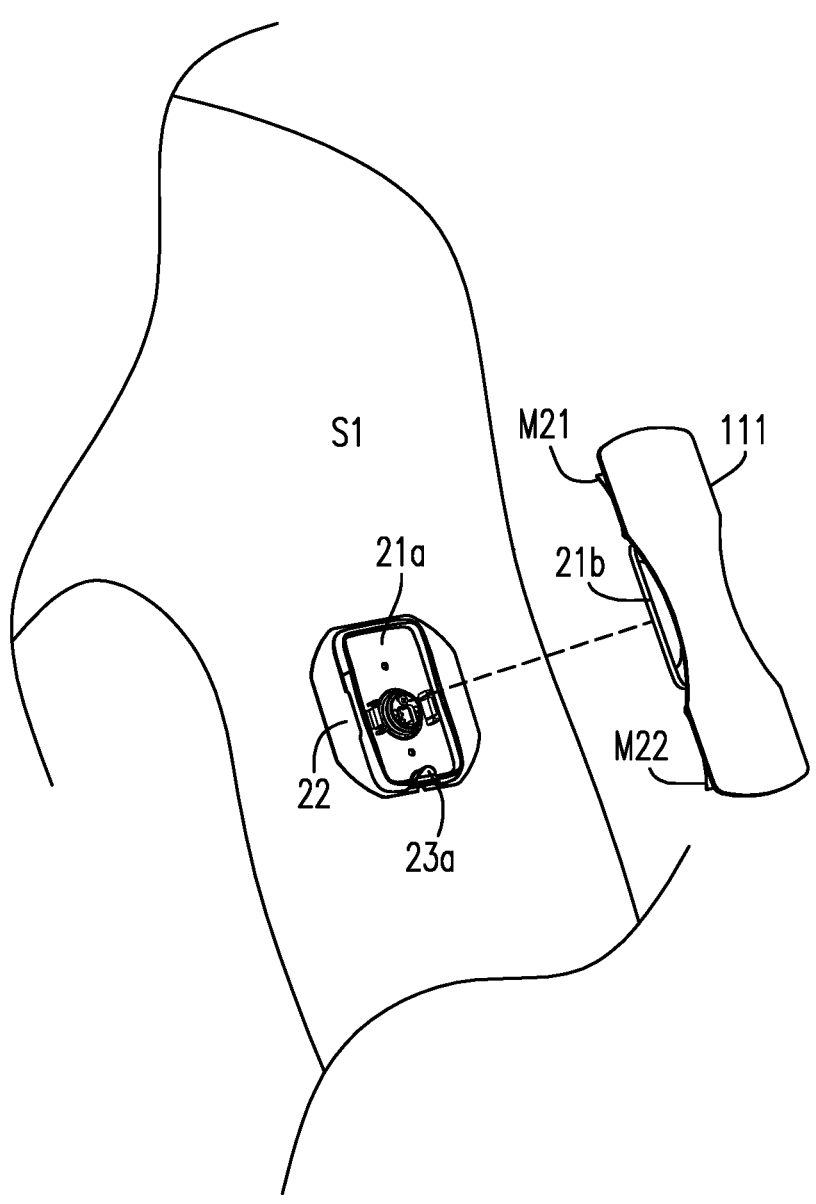
Figure 25E:
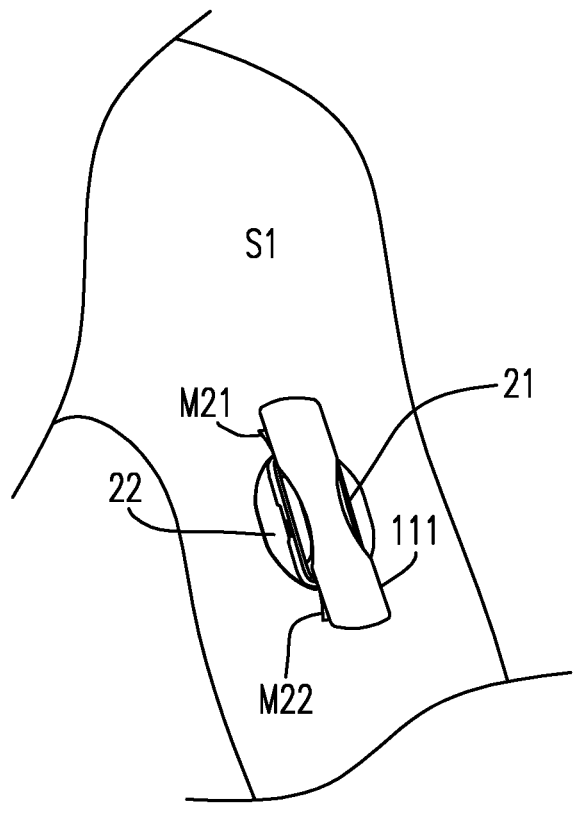
Figures 25F, 25G:
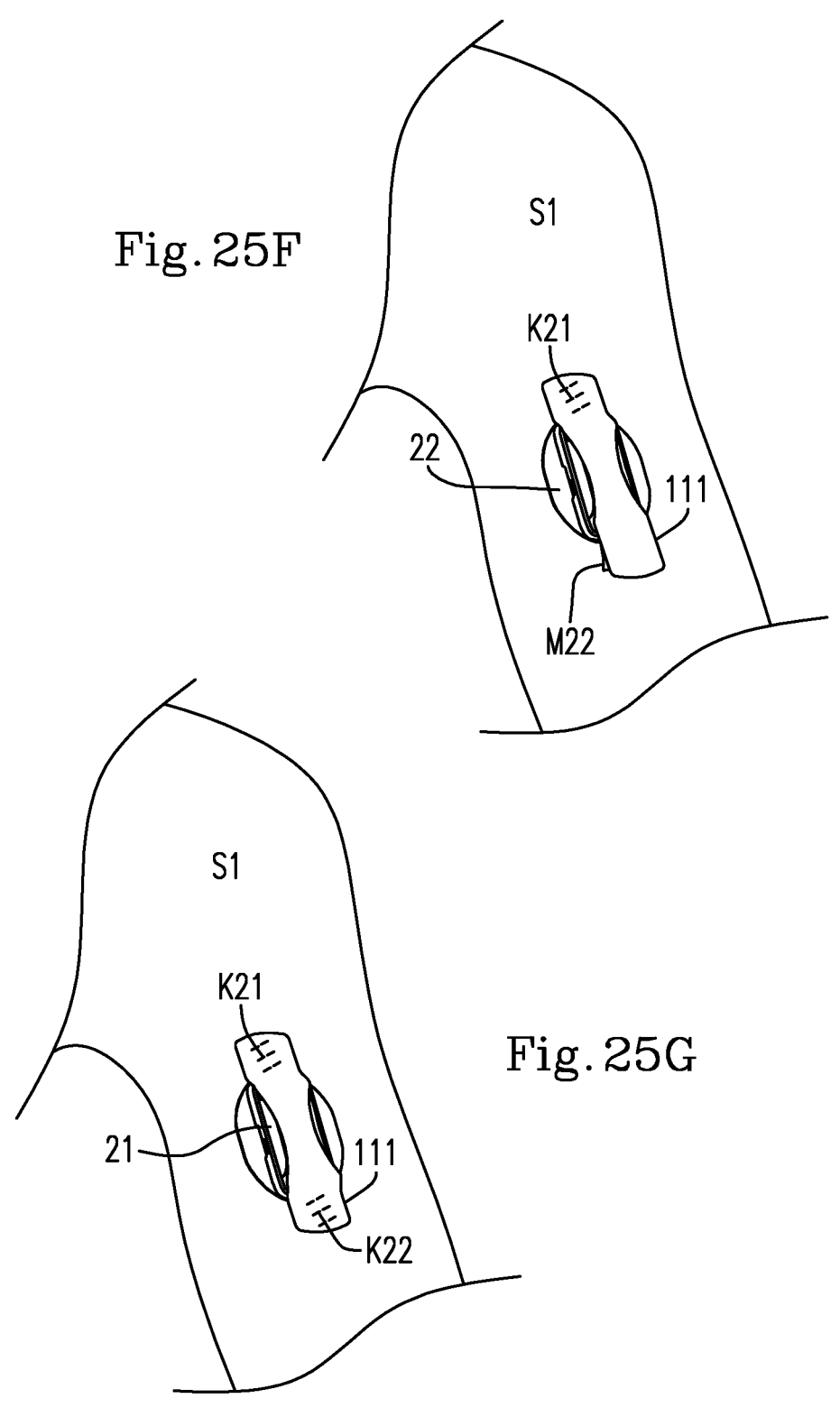

As shown in FIG. 25D, the transmitter 21b assembled with the patch 10 can utilize its fool-proof surface structure 23b to be aligned to the fool-proof surface structure 23a of the base 21a. As shown in FIG. 25E, the transmitter 21b is then installed to the base 21a. As shown in FIG. 25F, the outer peelable sub-portions N21 is peeled off by using the lifted first inner peelable sub-portion M21 as an auxiliary peeling part. Then, the first patch area K21 of the backing 111 is downward pressed to be adhered to the side Q22 of the transmitter 21b, the base 21a and the skin surface S1. As shown in FIG. 25G, the outer peelable sub-portions N22 is peeled off by using the second inner peelable sub-portion M22, which is lifted, as an auxiliary peeling part. Then, the second patch area K22 of the backing 111 is downward pressed to be adhered to the side Q22 of the transmitter 21b, the base 21a and the skin surface S1. Thus, the backing 111 is finished to be adhered to the physiological parameter detection device 21 and the skin surface S1.

A method W21 (or another installation method) for adhering the patch 10 to the physiological parameter detection device 21 is disclosed. The method W21 includes the following steps: A physiological parameter detection device 21 is provided, wherein the physiological parameter detection device 21 at least includes a base 21a and a transmitter 21b, the base 21a is disposed on the skin surface S1 with a base patch 22, and the transmitter 21b is detachably to be installed to the base 21a and has a top surface 21S. In addition, the base 21a is adhered to the skin surface S1 with the base patch 22.

The method W21 further includes the following steps: The first and the second inner peelable sub-portions M21 and M22 of the patch 10 are lifted with respect to the cutting line D2 to expose the central adhesive portion H1. The central adhesive portion H1 of the patch 10 is caused to be adhered to the top surface 21S of the transmitter 21b. The transmitter 21b adhered with the patch 10 is installed to the base 21a. In addition, the two outer peelable sub-portions N21 and N22 are peeled off by taking the first and the second inner peelable sub-portions M21 and M22 as force application points so as to allow the outer adhesive portion H2 to be adhered onto the physiological parameter detection device 21 and the skin surface S1.

Figure 26A:
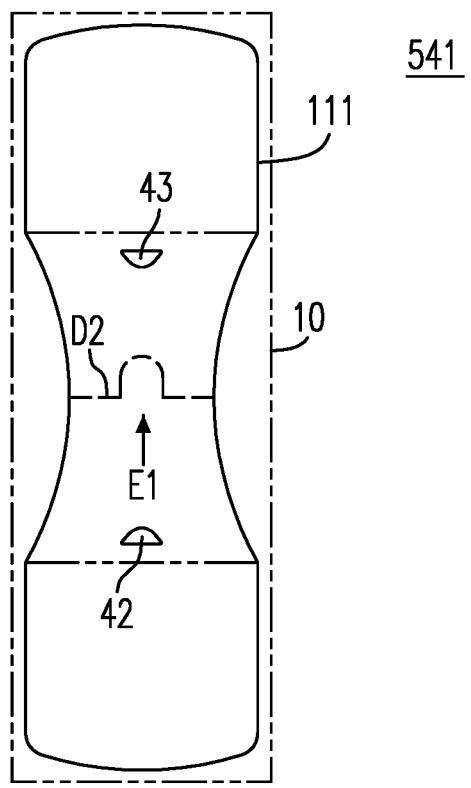
FIG. 26A shows a changed structure of the patch shown in FIG. 23A.
Figure 26B:
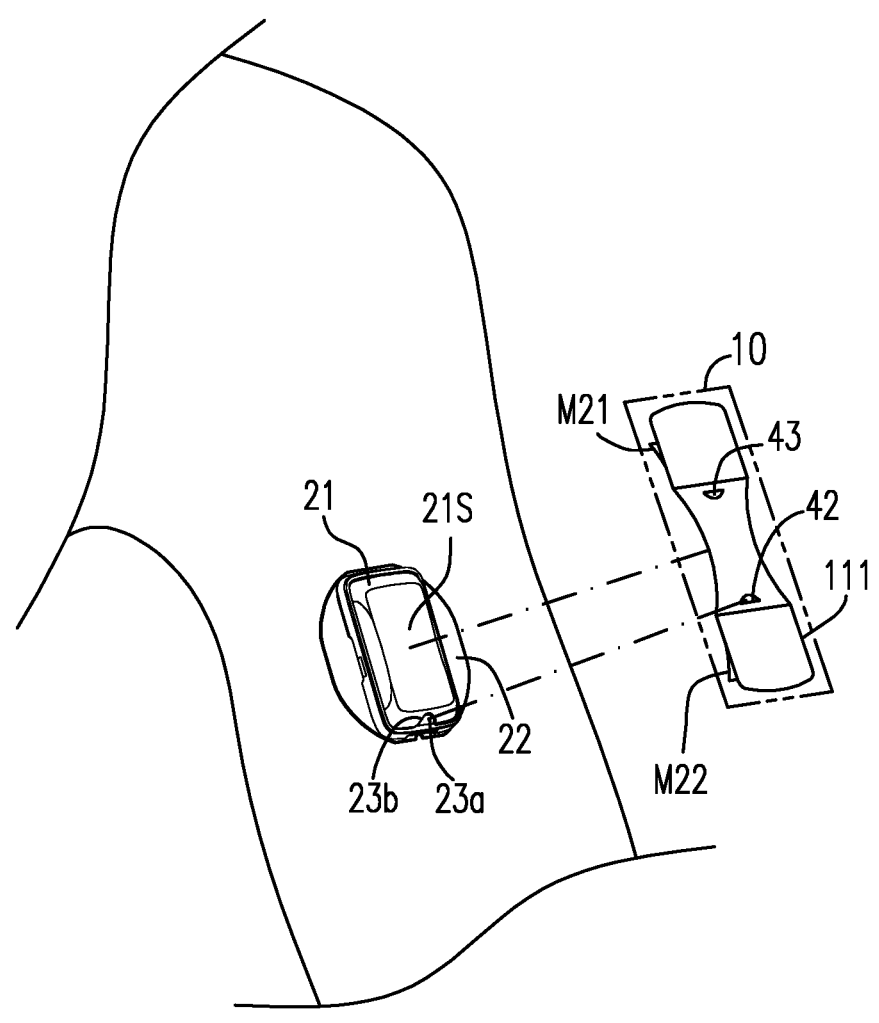
FIG. 26B, FIG. 26C and FIG. 26D respectively show an operation for the patch system using the patch of FIG. 26A.
Figure 26C:
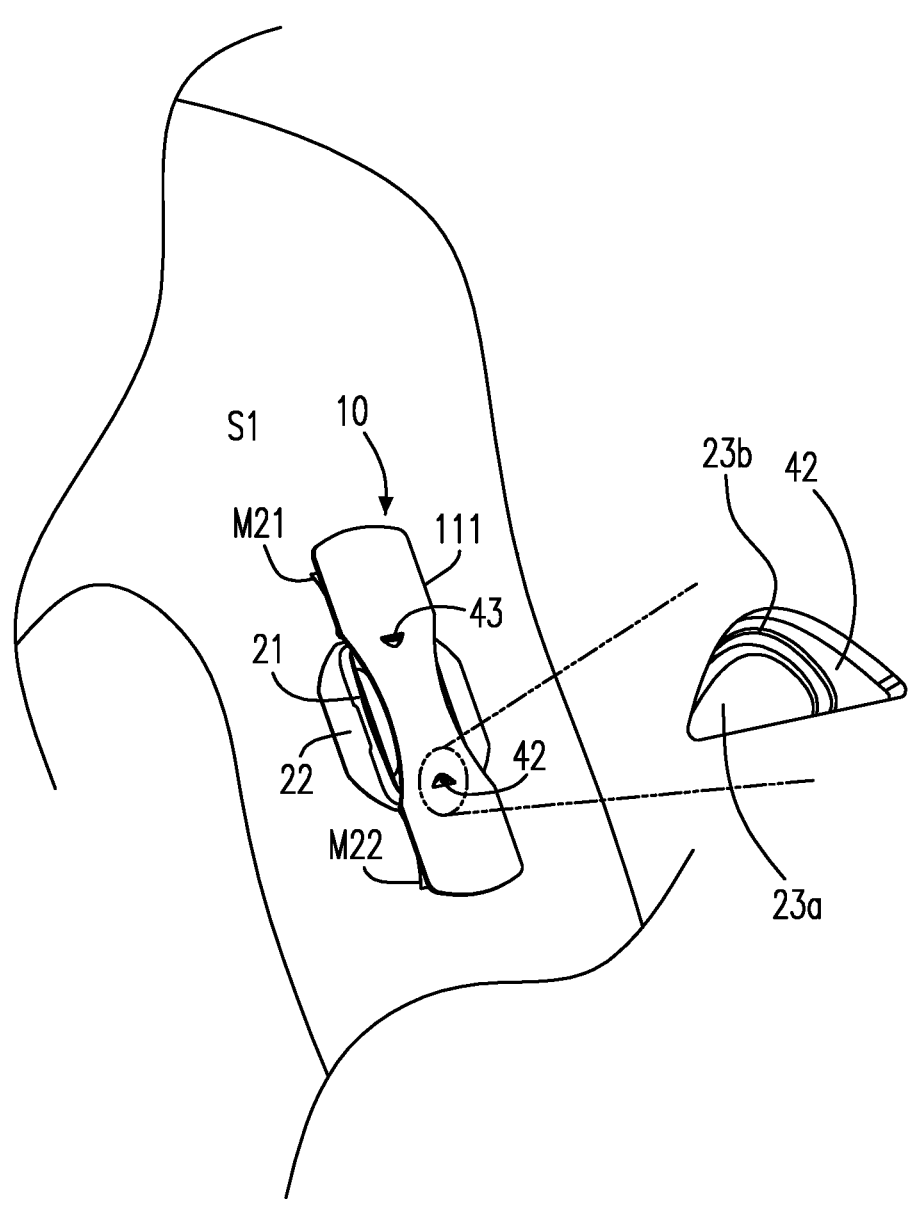
Figure 26D:
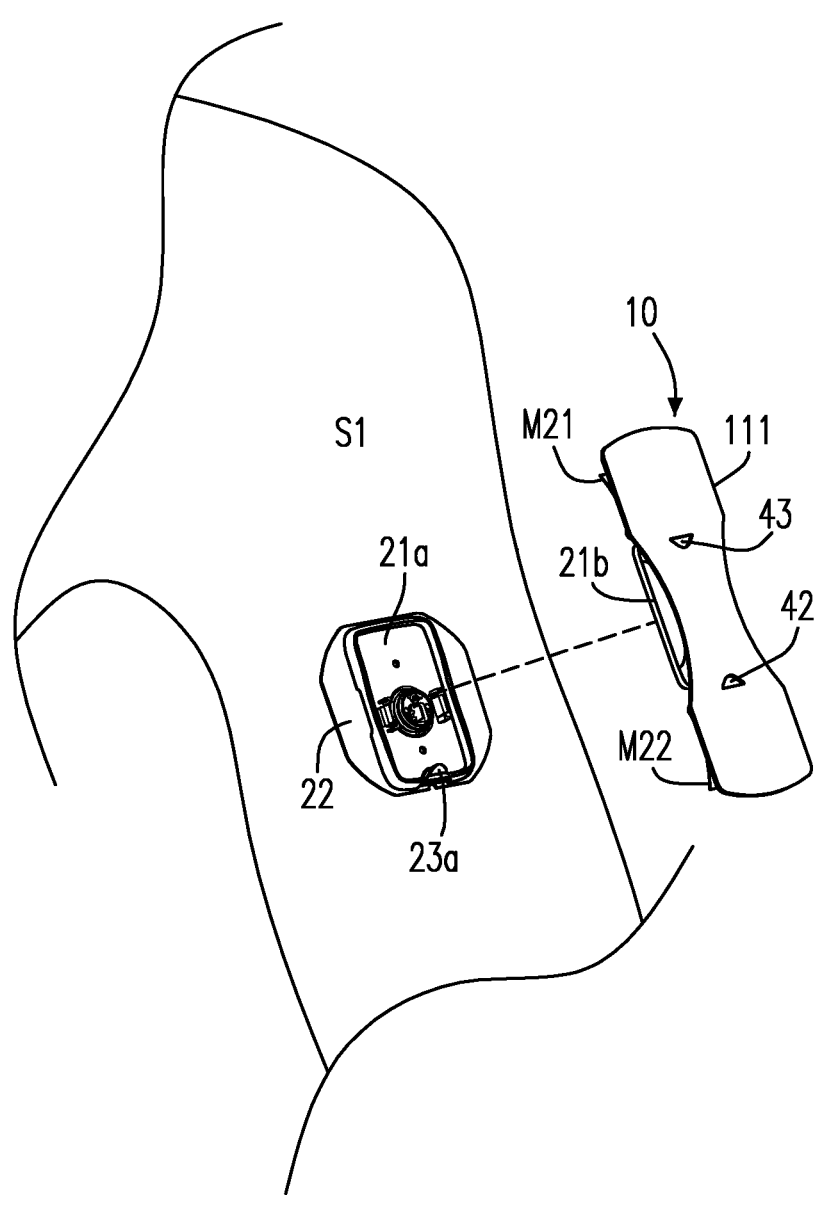

Please refer to FIG. 26A, FIG. 26B, FIG. 26C and FIG. 26D. FIG. 26A shows another implementation structure 541 of the patch 10 shown in FIG. 17. FIGS. 26B, 26C and 26D respectively show the patch system 7 using the implementation structure 541.

As shown in FIG. 26A, the implementation structure 541 is a changed structure of the implementation structure 521 of FIG. 23A. The backing 111 has a longitudinal direction E1, and has a relatively large ductility in the longitudinal direction E1. The central adhesive portion H1 is disposed along the longitudinal direction E1. The patch 10 includes at least one hole 42 passing through the backing 111. For example, the patch 10 disposes to have the hole 42 in the central adhesive portion H1. When the patch 10 is caused to apply the pressure P1 to the physiological parameter detection device 21, the hole 42 is configured to correspond to the fool-proof surface structure 23b of the transmitter 21b. In addition, the backing can further includes another hole 43. When the patch 10 is caused to apply the pressure P1 to the physiological parameter detection device 21, the hole 43 is configured to correspond to the short side Q22 of the transmitter 21b. More particularly, the hole 42 and the hole 43 are disposed opposite to each other.

The installation method for the patch 10 included in the implementation structure 541 may has two kinds. A first kind of installation method is shown in FIG. 26B and FIG. 26C. As shown in FIG. 26B, the base 21a is adhered to the skin surface S1 via the base patch 22, the transmitter 21b is disposed to the base 21a, and the central portion H1 is ready to be adhered to the top surface 21S of the transmitter 21b. In FIG. 26C, the central portion H1 is adhered to the top surface 21S of the transmitter 21b. The following steps for the first kind of installation method are the same as shown in FIG. 24E and FIG. 24F. That is, in the first kind of installation method, after the transmitter 21b is installed to the base 21a, the patch 10 is adhered onto the transmitter 21b.

A second kind of installation method is shown in FIG. 26D. In the beginning, the transmitter 21b is separated from the base 21a. The central adhesive portion H1 is adhered to the top surface 21S of the transmitter 21b, and the transmitter 21b adhered with the patch 10 is ready to be disposed to the base 21a. The following steps for the second kind of installation method are the same as shown in FIGS. 25E-25G. That is, in the second kind of installation method, before the transmitter 21b is installed to the base 21a, the central adhesive portion H1 of the patch 10 is adhered onto the top surface 21S of the transmitter 21b.

A method W31 for enhancing an adhesion strength of the physiological parameter detection device 21 to a skin surface S1 is disclosed. The physiological parameter detection device 21 includes a base 21a and a transmitter 21b. The base 21a is used to be disposed on the skin surface S1. The transmitter 21b is detachably installed to the base 21a, and has a top surface 21S.

The method W31 includes the following steps: A patch 10 including a backing 111 and a peelable sheet 12 is provided, wherein the backing 111 disposes thereon an adhesive layer 112 having an adhesive surface 113, the adhesive surface 113 includes a central adhesive portion H1 and an outer adhesive portion H2, the peelable sheet 12 is detachably adhered to the adhesive surface 113 for preserving the adhesive surface 113, provides a supporting force for the backing 111, and includes an inner peelable portion 12A and an outer peelable portion 12B. The inner peelable portion 12A is peeled off from the central adhesive portion H1 to at least expose the central adhesive portion H1. With the supporting force provided by the outer peelable portion 12B for the backing 111, the exposed central adhesive portion H1 is adhered to the top surface 21S of the transmitter 21b. Under a condition that the base 21a is disposed on the skin surface S1, the patch 10 and the transmitter 21b are together installed to the base 21a so as to finish assembly of the physiological parameter detection device 21. Under a condition that the patch 10 and the transmitter 21b are together installed to the base 21a, the outer peelable portion 12B is peeled off to expose the outer adhesive portion H2. In addition, the exposed outer adhesive portion H2 is adhered to the skin surface S1.

The patch 10 further includes at least one hole 41 passing through the backing 111. For example, the hole 41 is located in the central adhesive portion H1, or is located between the central adhesive portion H1 and the outer adhesive portion H2. The step of adhering the exposed central adhesive portion H1 to the top surface 21S of the transmitter 21b includes a sub-step that: when the patch 10 is caused to apply the pressure P1 to the physiological parameter detection device 21, the hole 41 is caused to correspond to the at least one side Q21 of the physiological parameter detection device 21. Preferably, the backing 111 can further include another hole 42 passing through the backing 111. The step of adhering the exposed central adhesive portion H1 to the top surface 21S of the transmitter 21b includes a sub-step that: when the patch 10 is caused to apply the pressure P1 to the physiological parameter detection device 21, the hole 42 is configured to correspond to the fool-proof surface structure 23b of the transmitter 21b.

The inner peelable portion 12A and the outer peelable portion 12B have a first cutting line A therebetween. The outer peelable portion 12B has at least one third cutting line C to include a plurality of outer peelable sub-sheets 124. The step of peeling off the outer peelable portion 12B to expose the outer adhesive portion H2 includes a sub-step that: the plurality of outer peelable sub-sheets 124 are sequentially peeled off.

The outer adhesive portion H2 is symmetrically disposed on two sides of the central adhesive portion H1, and includes a first patch area K21 and a second patch area K22. The outer peelable portion 12B has two outer peelable sub-portions N21 and N22 respectively corresponding to the first and the second patch areas K21 and K22. The inner peelable portion 12A corresponds to the central adhesive portion H1, and includes a first inner peelable sub-portion M21 and a second inner peelable sub-portion M22 which are separate mutually. The step of adhering the exposed central adhesive portion H1 to the top surface 21S of the transmitter 21b includes a sub-step that: under a condition that the first and the second inner peelable sub-portion M21 and M22 are lifted and the lifted first and the second inner peelable sub-portion M21 and M22 are respectively folded toward the two outer peelable sub-portions N21 and N22 to expose the central adhesive portion H1, the supporting force for the backing 111 can be continuously provided by using the two outer peelable sub-portions N21 and N22 so as to secure an effective attachment of the central adhesive portion H1 on the top surface 21S of the physiological parameter detection device 21.

The inner peelable portion 12A and the outer peelable portion 12B have at least one pre-pressing line U11 therebetween, and are connected with the at least one pre-pressing line U11. The step of peeling off the inner peelable portion 12A from the central adhesive portion H1 includes a sub-step that: the inner peelable portion 12A is lifted and is folded toward the outer peelable portion 12B with respect to the pre-pressing line U11 so as to expose the central adhesive portion H1.

Figure 27A:
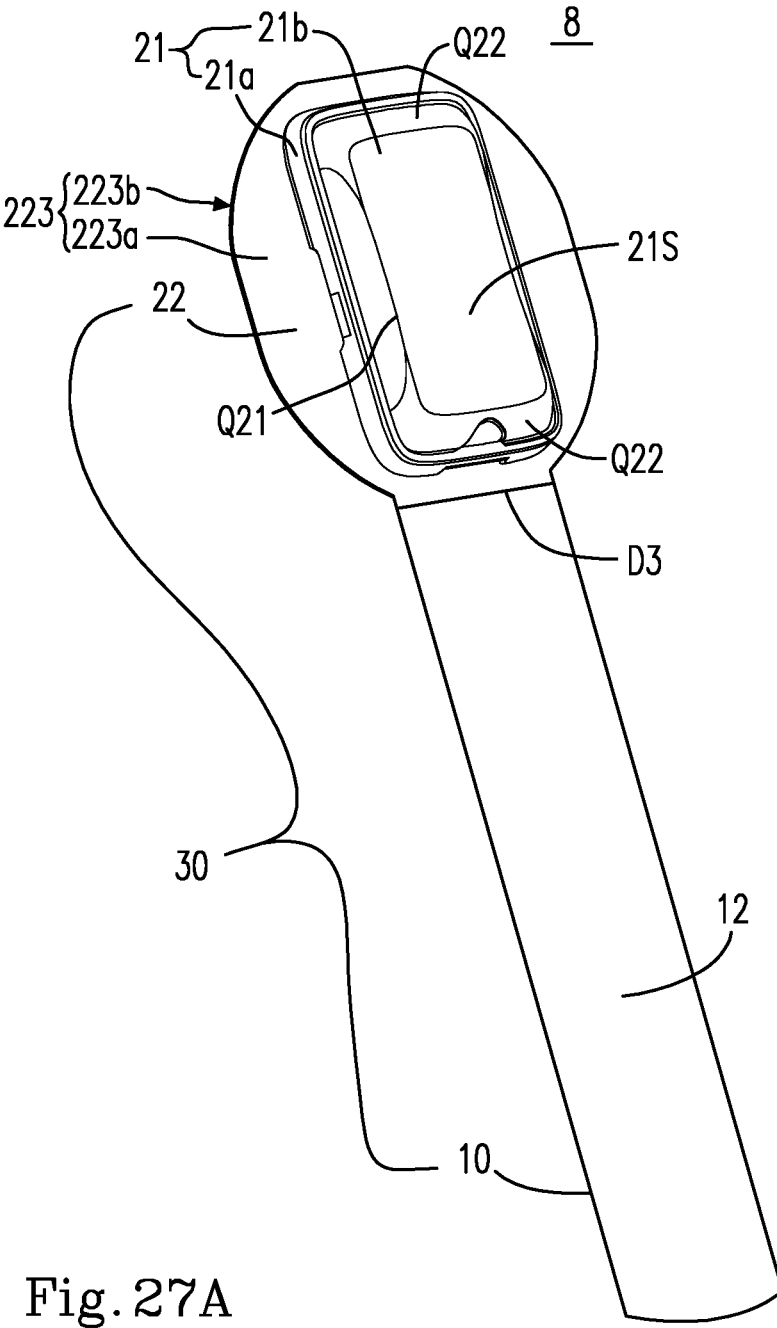
FIG. 27A shows a patch system according to another embodiment of the present invention.
Figure 27B:
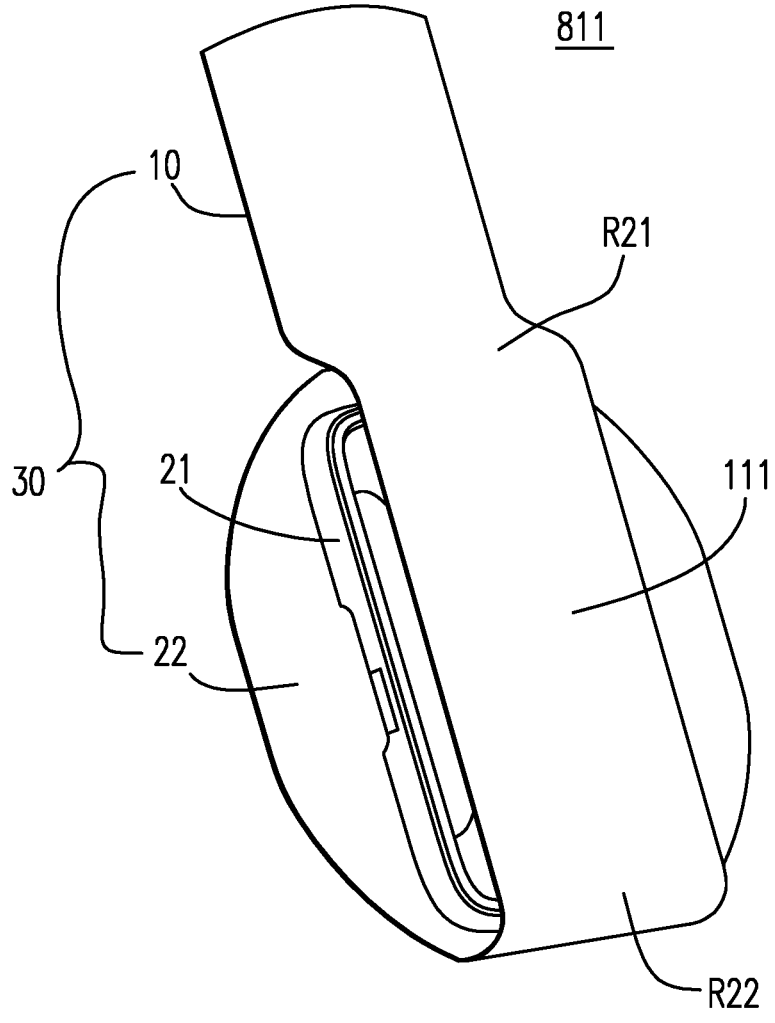
FIG. 27B shows an implementation structure of the patch system shown in FIG. 27A.

Please refer to FIG. 27A and FIG. 27B. FIG. 27A shows a patch system 8 according to an embodiment of the present invention. FIG. 27B shows an implementation structure 811 of the patch system 8 shown in FIG. 27A. As shown in FIG. 27A and FIG. 27B, the patch system 8 includes a physiological parameter detection device 21, and a patch assembly 30 associated with the physiological parameter detection device 21. The physiological parameter detection device 21 includes a base 21a and a transmitter 21b. The transmitter 21b is detachably assembled to the base 21a and has a top surface 21S, two long side Q21 and two short side Q22.

The patch assembly 30 is coupled to the physiological parameter detection device 21, and includes a base patch 22 (or a base patch portion 22) and a patch 10 (that is, one of a reinforcement patch 10 and a reinforcement patch portion 10) extending from the base patch 22. The base patch 22 has a backing 223, and the backing 223 has a coupling surface 223a and an adhesive surface 223b opposed to the coupling surface 223a. The coupling surface 223a of the backing 223 is configured to be coupled with the base 21a, and the adhesive surface 223b of the backing 223 is configured to be adhered to the skin surface (not shown in the figure). The patch 10 includes another backing 111, an adhesive layer 112 and a peelable sheet 12. The adhesive layer 112 has an adhesive surface 113. In particular, the backing 111 of the patch 10 is extended from the backing 223 of the base patch 22, that is, the patch 10 and the base patch 22 are integrally formed. The peelable sheet 12 is used to preserve the adhesive surface 113 of the patch 10. In addition, the adhesive surface 223b of the backing 223 is disposed opposite to the adhesive surface 113 of the patch 10.

The base 21a of the physiological parameter detection device 21 is disposed on the skin surface through the adhesive surface 223b of the base patch 22. The transmitter 21b is installed to the base 21a. Afterward, the peelable sheet 12 is separated from the coupling surface 223a of the base patch 22 via a fourth cutting line D3 so as to be removed. The adhesive surface 113 of the patch portion 10 is then folded toward the base patch 22; and the adhesive surface 113 is adhered along the side Q22, the top surface 21S and the other side Q22 to form at least two inclined surfaces R21 and R22. Although it is not shown in the figure, the peelable sheet 12 can include an inner peelable portion close to the coupling surface 223a of the base patch 22, and an outer peelable portion away from the coupling surface 223a of the base patch 22. The inner peelable portion and the outer peelable portion can be separated by another cutting line or connected through another pre-pressing line. As mentioned above, when the patch 10 is prepared to be adhered to the physiological parameter detection device 21, the inner peelable portion can be removed or lifted to expose a portion of the adhesive surface 113 so as to allow the patch 10 to be adhered onto a portion of the physiological parameter detection device 21, such as the side Q22 of the transmitter 21b. At this time, the remaining outer peelable portion will keep supporting the backing 111 so as to maintain the flatness of the patch 10.

Figure 28A:
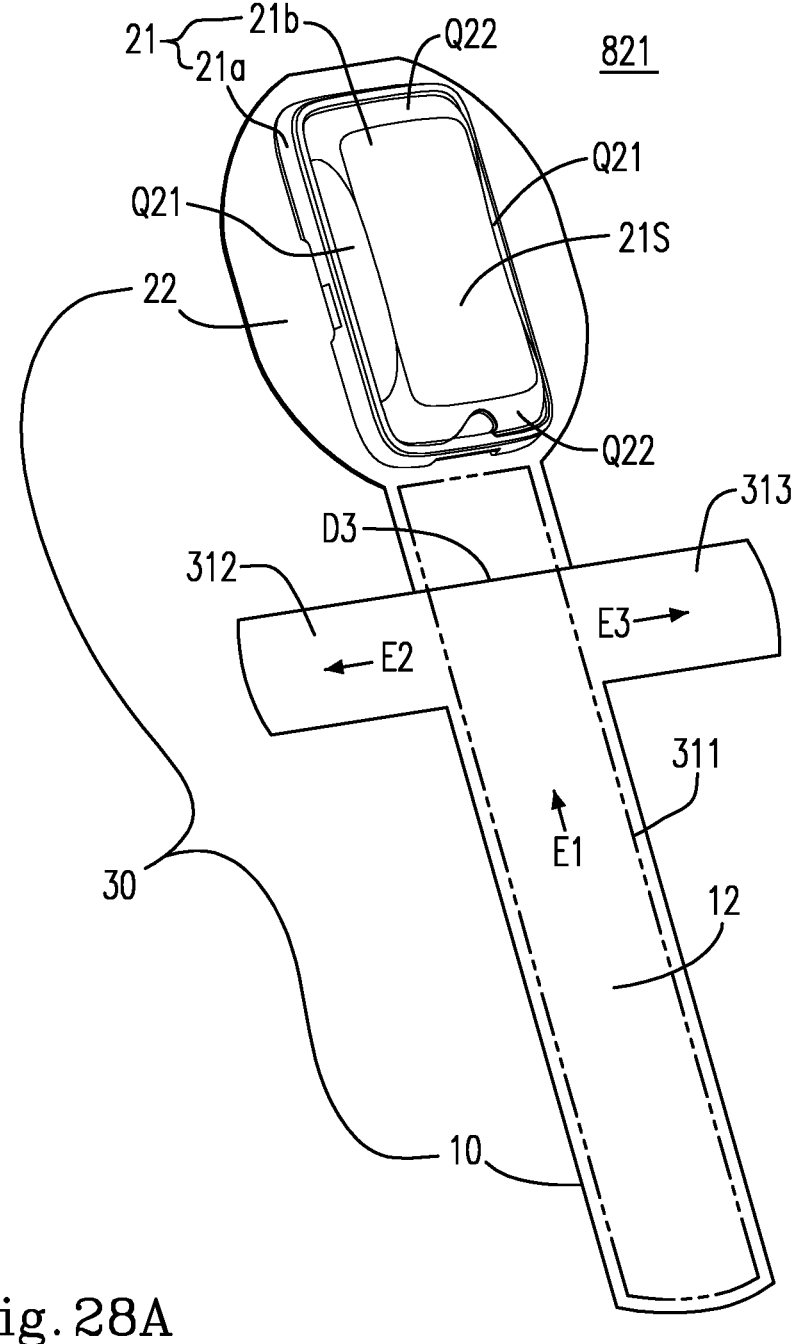
FIG. 28A and FIG. 28B respectively show another two implementation structures of the patch system shown in FIG. 27A.
Figure 28B:
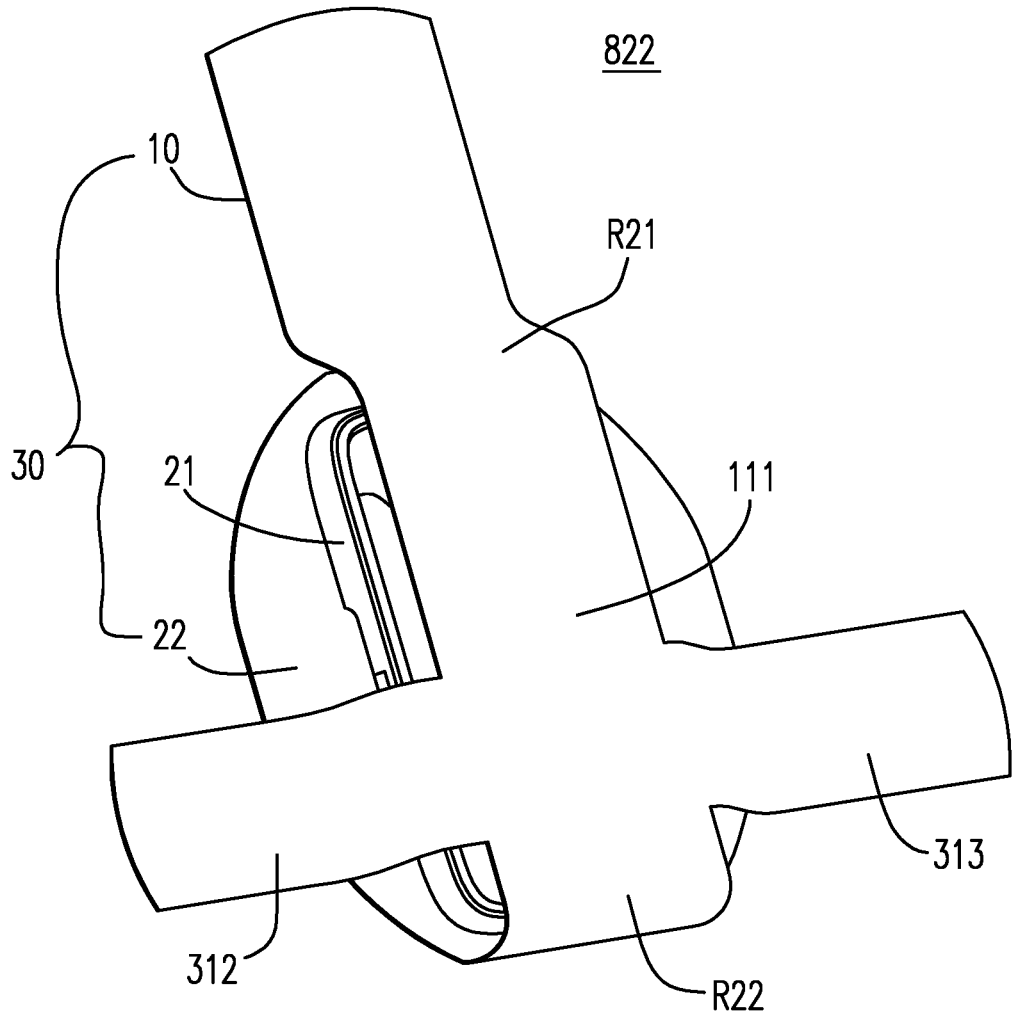

Please refer to FIG. 28A and FIG. 28B, which respectively show another two implementation structures 821 and 822 of the patch system 8 shown in FIG. 27A. As shown in FIG. 28A and FIG. 28B, the backing 111 has a longitudinal direction E1, a specific direction E2 being perpendicular to the longitudinal direction E1, and a specific direction E3 being opposite to the specific direction E3. The backing 111 has a main body portion 311 in the longitudinal direction E1, and has an extension portion 312 extending from the main body portion 311 in the specific direction E2. The backing 111 may further have an extension portion 313 extending from the main body portion 311 in the specific direction E3.

The extension portion 313 is aligned with the extension portion 312. For example, the extension portions 312 and 313 are two wing portions, respectively. Therefore, the patch 10 may preferably further include at least one wing portion. The at least one wing portion is used to provide a fixed direction (e.g., the specific direction E2) different from the longitudinal direction E1, and is used to raise a binding strength between an edge of the physiological parameter detection device 21 and the skin surface (not shown in the figure). For example, the location of the edge corresponds to a connection location between the base patch 22 and the patch 10.

In the implementation structure 822, the base patch 22 and the patch 10 is connected at the connection location on one side of the physiological parameter detection device 21. Therefore, the patch 10 is adhered along one short side Q22, the top surface 21S and another short side Q22 of the transmitter 21b, and extends outward to be adhered to the skin surface (not shown in the figure); in this way, the patch 10 provides a downward pressure to the whole of the physiological parameter detection device 21, and thus enhances an adhesion strength of the physiological parameter detection device 21 adhered to the skin surface (not shown in the figure).

What is claimed is:

1. A patch for increasing an adhesive strength of a physiological parameter detection device on a skin surface, wherein the physiological parameter detection device has a top surface and at least two longitudinal sides, the patch comprising:

a backing having disposed thereon an adhesive layer having an adhesive surface, wherein:

the adhesive surface includes a central adhesive portion and an outer adhesive portion; and when the central adhesive portion is exposed, the patch is configured to apply a pressure toward the physiological parameter detection device so as to allow the central adhesive portion to be adhered to the top surface of the physiological parameter detection device; and a peelable sheet detachably adhered to the adhesive surface for preserving the adhesive surface, and including an inner peelable portion and an outer peelable portion, wherein, after the central adhesive portion is exposed, the outer peelable sheet continuously provides a supporting force for the backing so as to allow the backing to be easily and evenly adhered, and wherein the backing has a longitudinal direction extending along an axis of the two longitudinal sides of the physiological parameter detection device and a specific direction being perpendicular to the longitudinal direction, a ductility of the backing in the longitudinal direction is larger than a ductility of the backing in the specific direction, and the central adhesive portion is disposed along the longitudinal direction.

2. The patch according to claim 1, further comprising at least one pair of holes passing through the backing, wherein:

the at least one pair of holes are disposed symmetrically with respect to the longitudinal direction in the central adhesive portion, the patch applies the pressure toward the physiological parameter detection device, and either of the holes is configured to be aligned with one of at least one side or at least one fool-proof surface structure of the physiological parameter detection device.

3. The patch according to claim 1, further comprising at least one pair of holes passing through the backing, wherein:

the at least one pair of holes are disposed symmetrically with respect to the longitudinal direction between the central adhesive portion and the outer adhesive portion, the patch applies the pressure toward the physiological parameter detection device, and either of the holes is configured to be aligned with one of at least one side or at least one fool-proof surface structure of the physiological parameter detection device.

4. The patch according to claim 1, wherein:

the outer adhesive portion surrounds the central adhesive portion and includes a first patch area and a second patch area;

the inner peelable portion of the peelable sheet corresponds to a combination of the central adhesive portion and the first patch area; and the outer peelable portion of the peelable sheet corresponds to the second patch area.

5. The patch according to claim 4, wherein:

the patch further comprises at least one pair of holes passing through the backing;

the inner peelable portion comprises a first inner peelable sub-portion and a second inner peelable sub-portion respectively corresponding to the central adhesive portion and the first patch area and separated by a fourth cutting line;

the outer peelable portion surrounds the second inner peelable sub-portion and the second inner peelable sub-portion surrounds the first inner peelable sub-portion;

a first cutting line is disposed between the second inner peelable sub-portion and the outer peelable portion; and when the first inner peelable sub-portion is peeled off, the central adhesive portion and the at least one pair of holes are exposed and the second inner peelable sub-portion and the outer peelable portion continuously provide the supporting force for the backing so as to allow the central adhesive portion to be easily adhered onto the top surface of the physiological parameter detection device.

6. The patch according to claim 1, wherein:

a first cutting line is disposed between the inner peelable portion and the outer peelable portion; and the outer peelable portion includes at least one third cutting line so as to have a plurality of outer peelable sub-sheets.

7. The patch according to claim 1, wherein:

the outer adhesive portion is symmetrically disposed on two sides of the central adhesive portion and includes a first patch area and a second patch area; and the outer peelable portion includes two outer peelable sub-portions respectively corresponding to the first and the second patch areas.

8. The patch according to claim 7, wherein:

the inner peelable portion corresponds to the central adhesive portion and includes a first inner peelable sub-portion and a second inner peelable sub-portion separated to each other; and when the first inner peelable sub-portion and the second inner peelable sub-portion are lifted and the lifted first and the second inner peelable sub-portion are respectively folded toward the two outer peelable sub-portions to expose the central adhesive portion, the two outer peelable sub-portions continuously provide the supporting force for the backing so as to allow the central adhesive portion to be easily adhered onto the top surface of the physiological parameter detection device.

9. The patch according to claim 8, wherein:

the first inner peelable sub-portion and the second inner peelable sub-portion of the inner peelable portion are separated by a fourth cutting line; and the fourth cutting line is a curve, a polyline or a straight line.

10. The patch according to claim 7, wherein:

the inner peelable portion corresponds to the central adhesive portion and is separated from at least one of the two outer peelable sub-portions through one side of the inner peelable portion; and when the inner peelable portion is lifted to expose the central adhesive portion, the two outer peelable sub-portions continuously provide the supporting force for the backing so as to allow the central adhesive portion to be easily adhered onto the top surface of the physiological parameter detection device.

11. The patch according to claim 7, wherein:

the inner peelable portion is connected with the outer peelable portion through at least one pre-pressing line; and the inner peelable portion is capable of being lifted and folded toward the outer peelable portion with respect to the pre-pressing line so as to expose the central adhesive portion.

12. The patch according to claim 1, wherein an adhesive force per unit area of the central adhesive portion is less than an adhesive force per unit area of the outer adhesive portion.

13. The patch according to claim 1, wherein a position alignment is performed between two sides of the central adhesive portion and the two longitudinal sides of the physiological parameter detection device.

14. The patch according to claim 1, further comprising:

an auxiliary tearing part disposed on an edge of the outer peelable portion, wherein the auxiliary tearing part is protrusive; and a cutting line is formed upon the outer peelable portion from an end of the auxiliary tearing part to the opposite end of the outer peelable portion along the longitudinal direction.

\* \* \* \* \*